(12) United States Patent
Gogolin

(10) Patent No.: US 11,272,973 B2
(45) Date of Patent: Mar. 15, 2022

(54) COLD PLASMA ELECTROSURGICAL APPARATUS WITH BENT TIP APPLICATOR

(71) Applicant: Bovie Medical Corporation, Clearwater, FL (US)

(72) Inventor: Gary G. Gogolin, Tampa, FL (US)

(73) Assignee: Apyx Medical Corporation, Clearwater, FL (US)

( * ) Notice: Subject to any disclaimer, the term of this patent is extended or adjusted under 35 U.S.C. 154(b) by 749 days.

(21) Appl. No.: 15/544,905

(22) PCT Filed: Jan. 26, 2016

(86) PCT No.: PCT/US2016/014991
§ 371 (c)(1),
(2) Date: Jul. 20, 2017

(87) PCT Pub. No.: WO2016/123147
PCT Pub. Date: Aug. 4, 2016

(65) Prior Publication Data
US 2018/0014869 A1   Jan. 18, 2018

Related U.S. Application Data

(60) Provisional application No. 62/108,561, filed on Jan. 28, 2015.

(51) Int. Cl.
*A61B 18/14*      (2006.01)
*A61B 18/04*      (2006.01)
(Continued)

(52) U.S. Cl.
CPC ........ *A61B 18/042* (2013.01); *A61B 18/1482* (2013.01); *A61B 2017/00309* (2013.01);
(Continued)

(58) Field of Classification Search
CPC ........ A61B 18/042; A61B 2018/00601; A61B 2018/1475; A61B 2018/00202; A61B 2017/00738; A61B 2018/00583
See application file for complete search history.

(56) References Cited

U.S. PATENT DOCUMENTS 1,813,902 A   7/1931  Bovie
2,435,442 A   2/1948  Gurewitsch
(Continued)

FOREIGN PATENT DOCUMENTS

DE   2429021 A1   1/1976
EP   0186369 A1   7/1986
(Continued)

OTHER PUBLICATIONS

International Search Report and Written Opinion for PCT Application No. PCT/US2016/014991; dated Mar. 24, 2016; eighteen (18) pages.

(Continued)

*Primary Examiner* — Jaymi E Della
(74) *Attorney, Agent, or Firm* — Gerald Hespos; Michael Porco; Matthew T. Hespos

(57) ABSTRACT

Electrosurgical apparatuses having bent tip applicators are provided. In one implementation, an electrosurgical apparatus includes an insulating outer tube having a longitudinal axis, a proximal end, and a distal end. An outer tube distal housing has its proximal end coupled to the distal end of the insulating outer tube. A distal end of the outer tube distal housing extends from the insulating outer tube at an acute angle relative to the longitudinal axis. The exemplary electrosurgical apparatus further includes an electrically conducting tube disposed within the insulating outer tube and moveable along the longitudinal axis of the insulating outer tube. An electrode is coupled to a distal end of the electrically conducting tube. The exemplary electrosurgical appa- (Continued)

ratus may include a knob coupled to the insulating outer tube to effect rotation of the outer tube distal housing in 360 degrees of rotation.

25 Claims, 16 Drawing Sheets

(51) Int. Cl.
    *A61B 18/00*         (2006.01)
    *A61B 17/00*         (2006.01)

(52) U.S. Cl.
    CPC ............ *A61B 2017/00738* (2013.01); *A61B 2017/00862* (2013.01); *A61B 2017/00867* (2013.01); *A61B 2018/00077* (2013.01); *A61B 2018/00083* (2013.01); *A61B 2018/00101* (2013.01); *A61B 2018/00196* (2013.01); *A61B 2018/00202* (2013.01); *A61B 2018/00601* (2013.01); *A61B 2018/00994* (2013.01); *A61B 2018/1405* (2013.01); *A61B 2018/1475* (2013.01); *H05H 2240/10* (2013.01); *H05H 2240/20* (2013.01)

(56) References Cited

U.S. PATENT DOCUMENTS

| | | | |
|---|---|---|---|
| 3,239,730 A | 3/1966 | George | |
| 3,801,766 A | 4/1974 | Morrison | |
| 4,127,110 A | 11/1978 | Bullara | |
| 4,196,734 A | 4/1980 | Harris | |
| 4,545,375 A | 10/1985 | Cline | |
| 4,580,562 A | 4/1986 | Goof et al. | |
| 4,619,258 A | 10/1986 | Pool | |
| 4,625,723 A | 12/1986 | Altnether et al. | |
| 4,632,109 A | 12/1986 | Paterson | |
| 4,708,137 A | 11/1987 | Tsukagoshi | |
| 4,827,927 A | 5/1989 | Newton | |
| 4,884,557 A | 12/1989 | Takehana et al. | |
| 4,905,691 A | 3/1990 | Rydell | |
| 4,930,494 A | 6/1990 | Takehana et al. | |
| 5,088,997 A | 2/1992 | Delahuerga et al. | |
| 5,098,430 A | 3/1992 | Fleenor | |
| 5,207,675 A | 5/1993 | Canady | |
| 5,256,138 A | 10/1993 | Burek et al. | |
| 5,257,451 A | 11/1993 | Edwards et al. | |
| 5,269,780 A | 12/1993 | Roos | |
| 5,306,238 A | 4/1994 | Fleenor | |
| 5,400,267 A | 3/1995 | Denen et al. | |
| 5,403,342 A | 4/1995 | Tovey et al. | |
| 5,425,375 A | 6/1995 | Chin et al. | |
| 5,445,635 A | 8/1995 | Denen et al. | |
| 5,449,356 A | 9/1995 | Walbrink et al. | |
| 5,514,157 A | 5/1996 | Nicholas et al. | |
| 5,626,575 A | 5/1997 | Crenner | |
| 5,647,869 A | 7/1997 | Goble et al. | |
| 5,651,780 A | 7/1997 | Jackson et al. | |
| 5,660,657 A | 8/1997 | Rajala et al. | |
| 5,693,042 A | 12/1997 | Boiarski et al. | |
| 5,693,044 A | 12/1997 | Cosmescu | |
| 5,697,909 A | 12/1997 | Eggers et al. | |
| 5,720,745 A * | 2/1998 | Farin ................ | A61B 18/042 128/898 |
| 5,743,880 A | 4/1998 | Hlavka | |
| 5,776,092 A | 7/1998 | Farin et al. | |
| 5,800,427 A | 9/1998 | Zamba | |
| 5,908,381 A | 6/1999 | Aznoian et al. | |
| 5,916,213 A | 6/1999 | Haissaguerre et al. | |
| 5,921,915 A | 7/1999 | Aznoian et al. | |
| 5,922,003 A | 7/1999 | Anctil et al. | |
| 6,017,340 A | 1/2000 | Cassidy et al. | |
| 6,063,081 A | 5/2000 | Mulier et al. | |
| 6,099,523 A | 8/2000 | Kim et al. | |
| 6,146,380 A | 11/2000 | Racz et al. | |
| 6,193,715 B1 | 2/2001 | Wrublewski et al. | |
| 6,225,593 B1 | 5/2001 | Howieson et al. | |
| 6,231,571 B1 | 5/2001 | Ellman et al. | |
| 6,293,945 B1 | 9/2001 | Parins et al. | |
| 6,293,960 B1 | 9/2001 | Ken | |
| 6,325,799 B1 | 12/2001 | Goble | |
| 6,391,027 B1 * | 5/2002 | Farin ................ | A61B 18/042 606/34 |
| 6,409,724 B1 | 6/2002 | Penny et al. | |
| 6,451,016 B1 | 9/2002 | Karakozian | |
| 6,458,125 B1 | 10/2002 | Cosmescu | |
| 6,475,215 B1 | 11/2002 | Tanrisever | |
| 6,508,815 B1 | 1/2003 | Strul et al. | |
| 6,558,383 B2 | 5/2003 | Cunningham et al. | |
| 6,578,579 B2 | 6/2003 | Burnside et al. | |
| 6,652,514 B2 | 11/2003 | Ellman et al. | |
| 6,740,079 B1 | 5/2004 | Eggers et al. | |
| 6,743,239 B1 | 6/2004 | Kuehn et al. | |
| 6,770,071 B2 | 8/2004 | Woloszko et al. | |
| 6,852,112 B2 | 2/2005 | Platt | |
| 6,899,538 B2 | 5/2005 | Matoba | |
| 6,958,063 B1 | 10/2005 | Soil et al. | |
| 6,994,707 B2 | 2/2006 | Ellman et al. | |
| 7,033,353 B2 | 4/2006 | Stoddard et al. | |
| 7,070,596 B1 | 7/2006 | Woloszko et al. | |
| 7,115,121 B2 | 10/2006 | Novak | |
| 7,156,842 B2 | 1/2007 | Sartor et al. | |
| 7,156,844 B2 | 1/2007 | Reschke et al. | |
| 7,169,144 B2 | 1/2007 | Hoey et al. | |
| 7,244,257 B2 | 7/2007 | Podhajsky et al. | |
| 7,306,614 B2 | 12/2007 | Weller et al. | |
| 7,316,682 B2 | 1/2008 | Konesky | |
| 7,335,199 B2 | 2/2008 | Goble et al. | |
| 7,354,435 B2 | 4/2008 | Farin et al. | |
| 7,422,585 B1 | 9/2008 | Eggers et al. | |
| 7,443,296 B2 | 10/2008 | Mezhinsky et al. | |
| 7,479,140 B2 | 1/2009 | Ellman et al. | |
| 7,481,809 B2 | 1/2009 | Stern et al. | |
| 7,503,917 B2 | 3/2009 | Sartor et al. | |
| 7,568,619 B2 | 8/2009 | Todd et al. | |
| 7,578,817 B2 | 8/2009 | Canady | |
| 7,654,975 B2 | 2/2010 | Mantell | |
| 7,749,221 B2 | 7/2010 | Rontal | |
| 7,815,638 B2 | 10/2010 | Farin et al. | |
| 8,016,824 B2 | 9/2011 | Buchman et al. | |
| 8,022,327 B2 | 9/2011 | Blomeyer | |
| 8,096,943 B2 | 1/2012 | Melville | |
| 8,177,782 B2 | 5/2012 | Beller et al. | |
| 8,216,220 B2 | 7/2012 | Jensen et al. | |
| 8,319,134 B2 | 11/2012 | Blomeyer | |
| 8,328,804 B2 | 12/2012 | Heard et al. | |
| 8,337,521 B2 | 12/2012 | Cooper et al. | |
| 8,353,905 B2 | 1/2013 | Jensen et al. | |
| 8,562,598 B2 | 10/2013 | Falkenstein et al. | |
| 8,568,400 B2 | 10/2013 | Gilbert | |
| 8,579,802 B2 | 11/2013 | Robertson | |
| 8,689,606 B2 | 4/2014 | Schellekens et al. | |
| 8,998,899 B2 | 4/2015 | Shilev et al. | |
| 9,005,112 B2 | 4/2015 | Hasser et al. | |
| 9,060,750 B2 | 6/2015 | Lam | |
| 9,060,765 B2 | 6/2015 | Rencher et al. | |
| 9,095,333 B2 | 8/2015 | Konesky et al. | |
| 9,144,453 B2 | 9/2015 | Rencher et al. | |
| 9,326,810 B2 | 5/2016 | Shilev et al. | |
| 9,492,219 B2 | 11/2016 | Konesky et al. | |
| 9,763,724 B2 | 9/2017 | Konesky et al. | |
| 9,770,281 B2 | 9/2017 | Rencher et al. | |
| 9,770,285 B2 | 9/2017 | Zoran et al. | |
| 10,064,675 B2 | 9/2018 | Rencher et al. | |
| 2001/0025177 A1 | 9/2001 | Woloszko et al. | |
| 2002/0013582 A1 | 1/2002 | Mulier et al. | |
| 2003/0018318 A1 * | 1/2003 | Melsky ............ | A61M 25/0138 604/526 |
| 2003/0018323 A1 | 1/2003 | Wallace et al. | |
| 2003/0050633 A1 | 3/2003 | Ellman et al. | |
| 2003/0130655 A1 | 7/2003 | Woloszko et al. | |
| 2004/0148903 A1 | 8/2004 | Cash | |
| 2004/0181150 A1 | 9/2004 | Evans et al. | |
| 2004/0243120 A1 | 12/2004 | Orszulak et al. | |

(56) References Cited

U.S. PATENT DOCUMENTS

| | | | |
|---|---|---|---|
| 2005/0075630 A1 | 4/2005 | Truckai et al. | |
| 2005/0113820 A1 | 5/2005 | Goble et al. | |
| 2005/0148903 A1 | 7/2005 | Diamantopoulos | |
| 2005/0267459 A1* | 12/2005 | Belhe | A61B 18/1492 606/41 |
| 2006/0036237 A1 | 2/2006 | Davison et al. | |
| 2006/0122595 A1 | 6/2006 | Farin et al. | |
| 2006/0161190 A1* | 7/2006 | Gadberry | A61B 17/29 606/174 |
| 2007/0028669 A1 | 2/2007 | Brewster | |
| 2007/0049922 A1 | 3/2007 | Rontal | |
| 2007/0049926 A1 | 3/2007 | Sartor | |
| 2007/0083247 A1 | 4/2007 | Wyeth et al. | |
| 2007/0093810 A1 | 4/2007 | Sartor et al. | |
| 2007/0135812 A1 | 6/2007 | Sartor | |
| 2007/0158209 A1 | 7/2007 | Kang et al. | |
| 2007/0260239 A1 | 11/2007 | Podhajsky et al. | |
| 2007/0270797 A1 | 11/2007 | Lu et al. | |
| 2007/0282303 A1* | 12/2007 | Nash | A61B 17/32037 604/510 |
| 2007/0282358 A1 | 12/2007 | Remiszewski et al. | |
| 2008/0071261 A1 | 3/2008 | Orszulak | |
| 2008/0108985 A1 | 5/2008 | Konesky | |
| 2008/0132893 A1 | 6/2008 | D'Amelio et al. | |
| 2008/0140066 A1 | 6/2008 | Davison et al. | |
| 2008/0300593 A1 | 12/2008 | Mulier et al. | |
| 2009/0005772 A1 | 1/2009 | Penny | |
| 2009/0125023 A1 | 5/2009 | Stephen et al. | |
| 2009/0143778 A1 | 6/2009 | Sartor et al. | |
| 2009/0149851 A1 | 6/2009 | Craig | |
| 2009/0248022 A1 | 10/2009 | Falkenstein et al. | |
| 2009/0253959 A1 | 10/2009 | Yoshie et al. | |
| 2009/0270796 A1 | 10/2009 | Perry et al. | |
| 2010/0016856 A1* | 1/2010 | Platt, Jr. | A61B 18/042 606/49 |
| 2010/0023008 A1 | 1/2010 | Heard et al. | |
| 2010/0094288 A1 | 4/2010 | Kerr | |
| 2010/0168827 A1 | 7/2010 | Schultz | |
| 2010/0262139 A1 | 10/2010 | Beller et al. | |
| 2011/0009856 A1 | 1/2011 | Jorgensen et al. | |
| 2011/0118601 A1 | 5/2011 | Barnes et al. | |
| 2011/0238053 A1 | 9/2011 | Brannan et al. | |
| 2011/0276113 A1 | 11/2011 | Cybulski | |
| 2012/0116397 A1* | 5/2012 | Rencher | A61B 18/1402 606/45 |
| 2012/0123405 A1 | 5/2012 | Moua et al. | |
| 2012/0197246 A1 | 8/2012 | Mauch | |
| 2012/0232540 A1 | 9/2012 | Baur et al. | |
| 2012/0330305 A1 | 12/2012 | Zoran et al. | |
| 2012/0330307 A1 | 12/2012 | Ladtkow et al. | |
| 2013/0046290 A1 | 2/2013 | Palmer et al. | |
| 2013/0237982 A1* | 9/2013 | Rencher | A61B 18/10 606/39 |
| 2013/0253498 A1* | 9/2013 | Germain | A61B 90/08 606/28 |
| 2013/0296846 A1 | 11/2013 | Canady et al. | |
| 2014/0005665 A1 | 1/2014 | Konesky et al. | |
| 2014/0018795 A1 | 1/2014 | Shilev et al. | |
| 2014/0236144 A1* | 8/2014 | Krueger | A61B 18/1477 606/41 |
| 2014/0257276 A1 | 9/2014 | Sartor | |
| 2015/0038790 A1 | 2/2015 | Rontal et al. | |
| 2015/0088060 A1 | 3/2015 | Wang et al. | |
| 2015/0209047 A1 | 7/2015 | Whitman | |
| 2016/0022347 A1 | 1/2016 | Rencher et al. | |
| 2016/0228171 A1 | 8/2016 | Boudreaux | |
| 2017/0273733 A1 | 9/2017 | Weber | |
| 2018/0146925 A1 | 5/2018 | Mogul | |

FOREIGN PATENT DOCUMENTS

| | | |
|---|---|---|
| EP | 0878263 A1 | 11/1998 |
| EP | 1764057 A1 | 3/2007 |
| EP | 1764057 B1 | 4/2009 |
| EP | 2263728 A2 | 12/2010 |
| EP | 2449992 A1 | 5/2012 |
| WO | 03082134 A1 | 10/2003 |
| WO | 2004096315 A2 | 11/2004 |

OTHER PUBLICATIONS

European Search Report for European Application No. 16743993.4; dated Aug. 24, 2018; nine (9) pages.

Office Action for Chinese Application No. 201680007798.X; dated Sep. 3, 2019; eleven (11) pages.

English Translation of Office Action for Chinese Application No. 201680007798 X; dated Sep. 3, 2019; fifteen (15) pages.

Office Action for Chinese Application No. 201680007798.X; dated Jun. 1, 2020; fourteen (14) pages.

English Translation of Office Action for Chinese Application No. 201680007798 X; dated Jun. 1, 2020; twelve (12) pages.

* cited by examiner

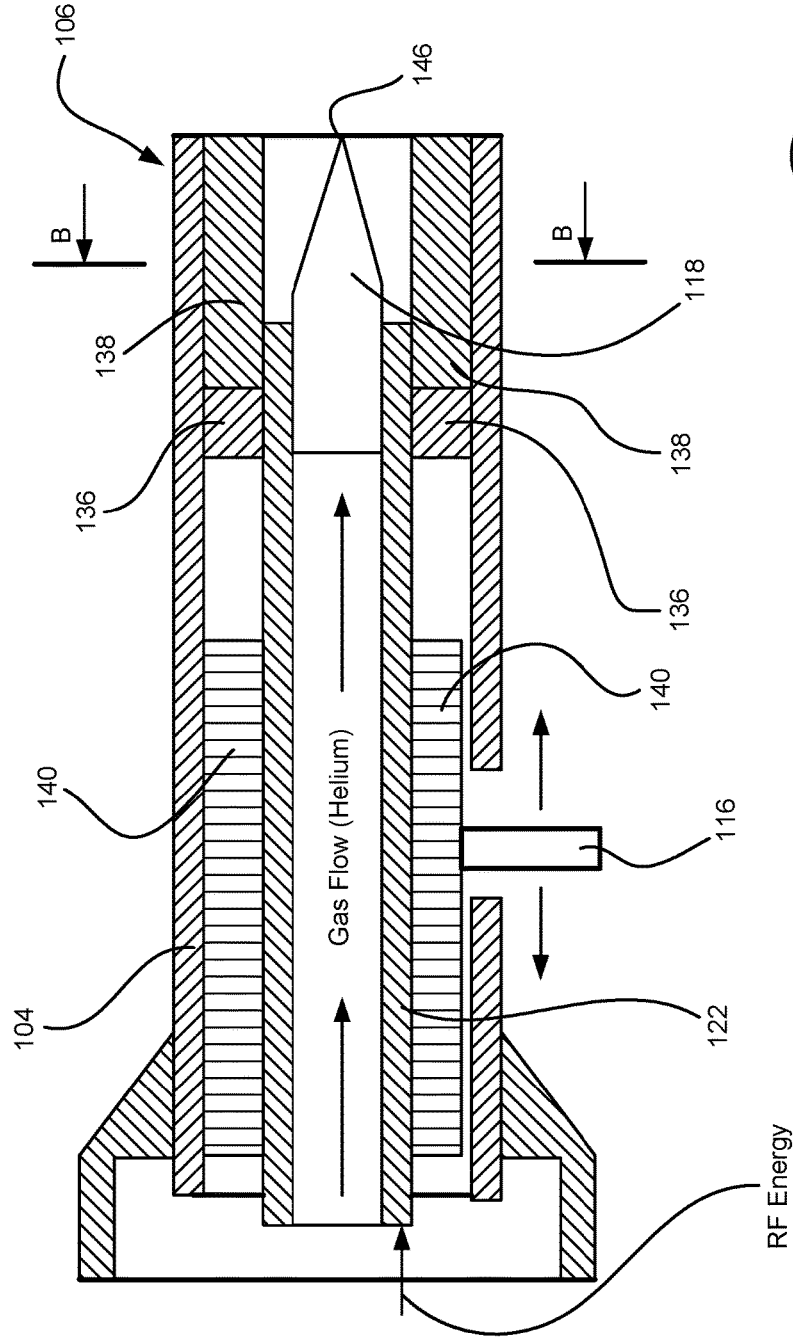
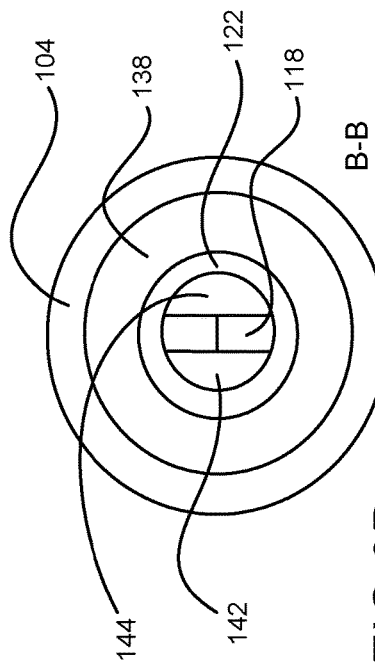
FIG.3A
FIG.3B

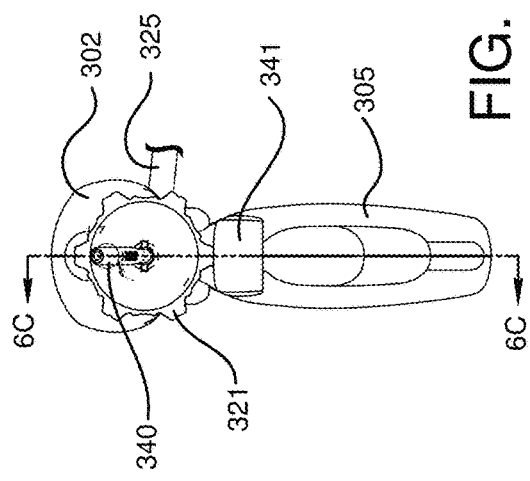
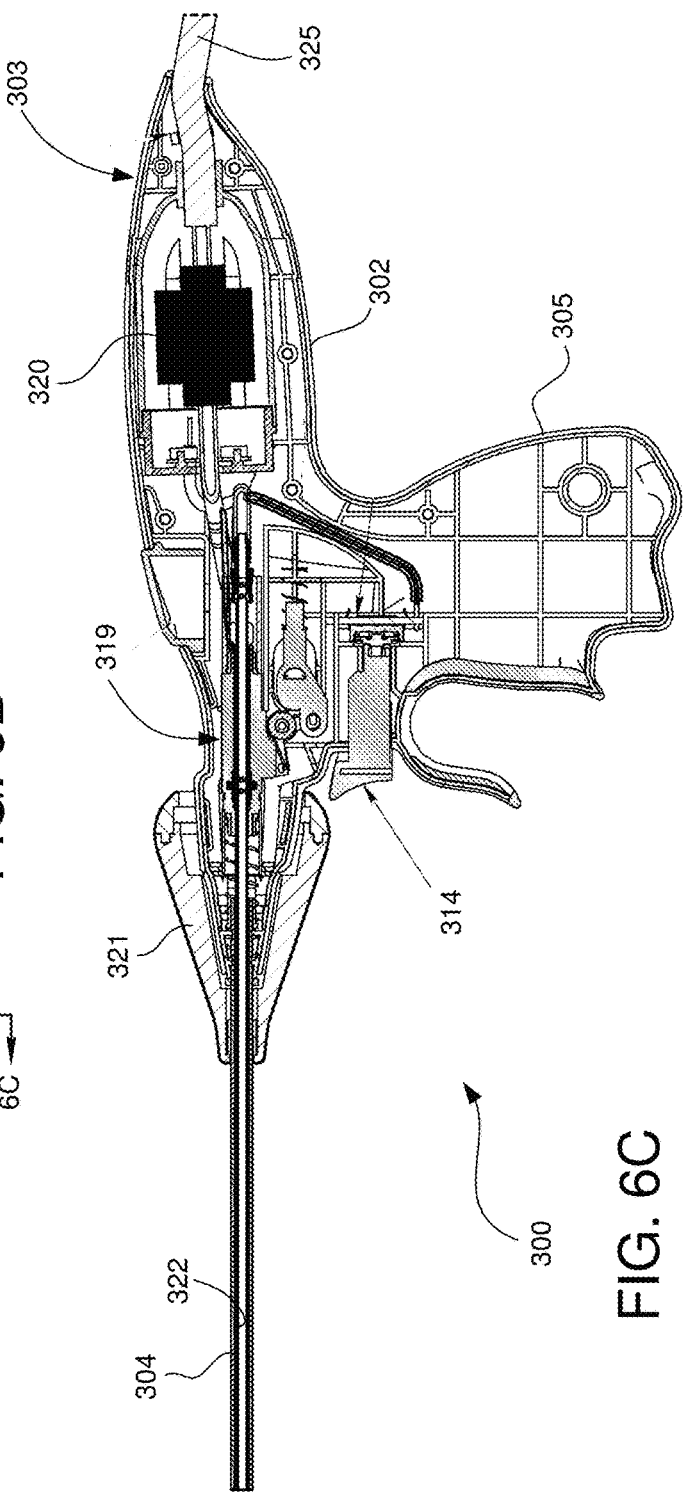
FIG. 6B
FIG. 6C

COLD PLASMA ELECTROSURGICAL APPARATUS WITH BENT TIP APPLICATOR

CROSS REFERENCE TO RELATED APPLICATIONS

This application claims priority to U.S. Provisional Patent Appl. No. 62/108,561, filed Jan. 28, 2015, entitled "COLD PLASMA ELECTROSURGICAL APPARATUS WITH BENT TIP APPLICATOR", the contents of which are hereby incorporated by reference in its entirety.

BACKGROUND

Field

The present disclosure relates generally to electrosurgery and electrosurgical systems and apparatuses, and more particularly, to an electrosurgical apparatus with a retractable blade for use in cold plasma applications, electrosurgical cutting and mechanical cutting.

Description of the Related Art

High frequency electrical energy has been widely used in surgery and is commonly referred to as electrosurgical energy. Tissue is cut and bodily fluids are coagulated using electrosurgical energy.

Electrosurgical instruments generally comprise "monopolar" devices or "bipolar" devices. Monopolar devices comprise an active electrode on the electrosurgical instrument with a return electrode attached to the patient. In monopolar electrosurgery, the electrosurgical energy flows through the active electrode on the instrument through the patient's body to the return electrode. Such monopolar devices are effective in surgical procedures where cutting and coagulation of tissue are required and where stray electrical currents do not pose a substantial risk to the patient.

Bipolar devices comprise an active electrode and a return electrode on the surgical instrument. In a bipolar electrosurgical device, electrosurgical energy flows through the active electrode to the tissue of a patient through a short distance through the tissue to the return electrode. The electrosurgical effects are substantially localized to a small area of tissue that is disposed between the two electrodes on the surgical instrument. Bipolar electrosurgical devices have been found to be useful with surgical procedures where stray electrical currents may pose a hazard to the patient or where other procedural concerns require close proximity of the active and return electrodes. Surgical operations involving bipolar electrosurgery often require methods and procedures that differ substantially from the methods and procedures involving monopolar electrosurgery.

Gas plasma is an ionized gas capable of conducting electrical energy. Plasmas are used in surgical devices to conduct electrosurgical energy to a patient. The plasma conducts the energy by providing a pathway of relatively low electrical resistance. The electrosurgical energy will follow through the plasma to cut, coagulate, desiccate, or fulgurate blood or tissue of the patient. There is no physical contact required between an electrode and the tissue treated.

Electrosurgical systems that do not incorporate a source of regulated gas can ionize the ambient air between the active electrode and the patient. The plasma that is thereby created will conduct the electrosurgical energy to the patient, although the plasma arc will typically appear more spatially dispersed compared with systems that have a regulated flow of ionizable gas.

Atmospheric pressure discharge cold plasma applicators have found use in a variety of applications including surface sterilization, hemostasis, and ablation of tumors. Often, a simple surgical knife is used to excise the tissue in question, followed by the use of a cold plasma applicator for cauterization, sterilization, and hemostasis. Cold plasma beam applicators have been developed for both open and endoscopic procedures. In the latter case, it is often desirable to be able to redirect the position of the cold plasma beam tip to a specific operative site. The external incision and pathway for the endoscopic tool may be chosen to avoid major blood vessels and non-target organs, and may not coincide with an optimum alignment for the target internal tissue site. A means of redirecting the cold plasma beam is essential in these situations.

Elaborate mechanisms have been developed to change the direction of the plasma beam by the surgeon as needed. However, these mechanisms are mechanically complicated, expensive to produce and, in some cases, unwieldy to operate effectively. The small diameter of the endoscopic trocar through which this surgical tool must be inserted places even more severe restrictions on these issues.

SUMMARY

The present disclosure relates to an electrosurgical apparatus with a retractable electrode, e.g., a blade, needle, sharp electrode, etc., for use in cold plasma applications, electrosurgical cutting and mechanical cutting. The electrosurgical apparatus includes a bent tip applicator for directing a cold plasma beam.

A simplified, low cost, and effective alternate approach for directing a cold plasma beam is described, where the cold plasma applicator tip is pre-bent to a desired angle and rotatable, i.e., roticulating. A shape-memory effect enables the tip of the applicator to be straightened somewhat while the tip passes through, for example, a trocar, and then resume a large portion of the original bend angle when the applicator tip arrives at the internal operative site. The bent tip can then be externally rotated by a surgeon to more accurately be directed to the target tissue. The tip bend angle can be externally adjusted by the surgeon multiple times.

The cold plasma beam is formed by passing an inert gas, such as helium or argon, over a sharp point that is held at high voltage and high frequency. The sharp point can take the form of an electrode, e.g., a surgical blade, needle electrode, a wire, etc., which can be extended or retracted from the bent tip applicator. When the electrode, e.g. a blade, is extended, it can be used as a standard endoscopic scalpel to make incisions, perform biopsies, and so on. When it is retracted, the blade serves as the sharp point to generate the cold plasma beam, which can then be used to seal the incision, perform hemostasis, and sterilize the operative site. In an additional operational mode, the blade or electrode can be extended and electrically energized while the inert gas is flowing over the blade or electrode, producing a gas-assisted electrosurgical cutting mode. This mode significantly improves the ease of cutting of the surgical blade, and the cooling effect of the flowing gas also substantially reduces, and in some cases eliminates, the formation of eschar.

According to one embodiment, an electrosurgical apparatus is provided and includes a housing having a passage extending therethrough. The housing also has a proximal end and a distal end. The electrosurgical apparatus further comprises an electrically conducting tube having a proximal end and a distal end. At least the proximal end of the electrically conducting tube is disposed in the passage of the housing. An insulating outer tube having a proximal end and a distal end is disposed around the electrically conducting tube with the proximal end of the insulating outer tube coupled to the distal end of the housing. The electrically conducting tube is movable along a longitudinal axis of the housing and insulating outer tube. The electrosurgical apparatus further includes an electrode coupled to the distal end of the electrically conducting tube. In a first position for electrosurgical cutting, the electrode extends beyond the distal end of the insulating outer tube and, in a second position, the electrode is retracted within the insulating outer tube and is energized via the electrically conducting tube to form plasma when an inert gas flows through the electrically conducting tube. The respective distal ends of the electrically conducting tube and the insulating outer tube are configured at a predetermined acute angle with respect to the longitudinal axis of the housing and insulating outer tube.

In one aspect, the electrosurgical apparatus includes a spring configured to electrically and mechanically couple the electrode to the distal end of the electrically conducting tube.

In another aspect, a flexible tube is disposed over the spring, the flexible tube configured to prevent gas leakage.

In yet another aspect, a portion of the distal end of the electrically conducting tube includes a plurality of cuts to enable articulation.

In another aspect, a flexible tube is disposed over the plurality of cuts of the electrically conducting tube to prevent gas leakage from the electrically conducting tube.

In one aspect, the distal end of the insulating outer tube is configured from a shape memory material.

In another aspect, the electrosurgical apparatus includes a slider member coupled to the electrically conducting tube for moving the electrically conducting tube along the longitudinal axis thereby extending and retracting the electrode.

In another aspect, the electrosurgical apparatus includes a knob coupled to the insulating outer tube to effect rotation of the distal end of the insulating outer tube in 360 degrees of rotation.

According to another embodiment, an electrosurgical apparatus comprises an insulating outer tube having a longitudinal axis, a proximal end, and a distal end. The electrosurgical apparatus further comprises an outer tube distal housing having a proximal end and a distal end. The proximal end of the outer tube distal housing is coupled to the distal end of the insulating outer tube. The distal end of the outer tube distal housing extends from the insulating outer tube at an acute angle. The electrosurgical apparatus also includes an electrically conducting tube having a proximal end and a distal end. The electrically conducting tube is disposed within the insulating outer tube and is moveable along the longitudinal axis of the insulating outer tube. An electrode is coupled to the distal end of the electrically conducting tube, wherein, in a first position, the electrode is disposed within the outer tube distal housing and, in a second position, the electrode extends at least partially beyond the distal end of the outer tube distal housing.

In one aspect, the electrically conducting tube includes a plurality of cuts to enable articulation.

In another aspect, the outer tube distal housing comprises a shape memory polymer that when stressed enables the outer tube distal housing to be at an angle other than the acute angle and when unstressed enables the outer tube distal housing to return to approximately the acute angle.

In another aspect, the electrosurgical apparatus includes a slider assembly coupled to the electrically conducting tube for moving the electrically conducting tube along the longitudinal axis of the insulating outer tube to thereby extend and retract the electrode.

In another aspect, the electrosurgical apparatus includes a knob coupled to the insulating outer tube to effect rotation of the outer tube distal housing in 360 degrees of rotation.

BRIEF DESCRIPTION OF THE DRAWINGS

The above and other aspects, features, and advantages of the present disclosure will become more apparent in light of the following detailed description when taken in conjunction with the accompanying drawings in which:

FIG. 3A is an enlarged cross sectional view of the electrosurgical apparatus in accordance with an embodiment of the present disclosure;

FIG. 3B illustrates a front view of the electrosurgical apparatus shown in FIG. 3A taken along line B-B;

FIG. 6B is a front view of the electrosurgical apparatus shown in FIG. 6A;

FIG. 6C is a cross sectional view of the electrosurgical apparatus shown in FIG. 6B taken along line 6C-6C;

FIG. 8D is a cross sectional view of the electrosurgical apparatus shown in

FIG. 8C taken along line 8D-8D;

FIG. 10A illustrates a distal end of the electrosurgical apparatus before insertion into a trocar, FIG. 10B illustrates the distal end of the electrosurgical apparatus passing through the trocar, and FIG. 10C illustrates the distal end of the applicator emerging from the distal end of the trocar when fully inserted.

Figure 1:
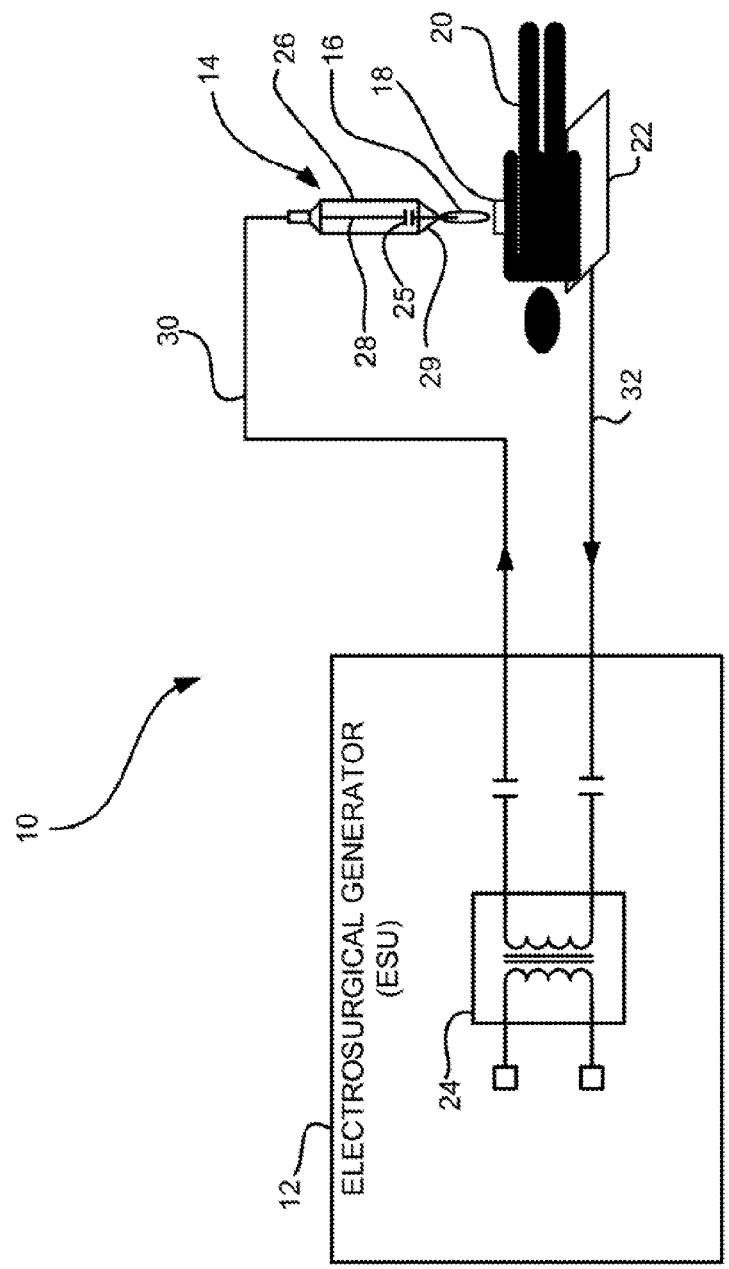
FIG. 1 is an illustration of an exemplary monopolar electrosurgical system in accordance with an embodiment of the present disclosure.

It should be understood that the drawings are for purposes of illustrating the concepts of the disclosure and are not necessarily the only possible configuration for illustrating the disclosure.

DETAILED DESCRIPTION

Preferred embodiments of the present disclosure will be described hereinbelow with reference to the accompanying drawings. In the following description, well-known functions or constructions are not described in detail to avoid obscuring the present disclosure in unnecessary detail. In the drawings and in the description which follow, the term "proximal", as is traditional, will refer to the end of the device, e.g., instrument, apparatus, applicator, handpiece, forceps, etc., which is closer to the user, while the term "distal" will refer to the end which is further from the user. Herein, the phrase "coupled" is defined to mean directly connected to or indirectly connected with through one or more intermediate components. Such intermediate components may include both hardware and software based components.

FIG. 1 shows an exemplary monopolar electrosurgical system generally indicated as 10 comprising an electrosurgical generator (ESU) generally indicated as 12 to generate power for the electrosurgical apparatus 10 and a plasma generator generally indicated as 14 to generate and apply a plasma stream 16 to a surgical site or target area 18 on a patient 20 resting on a conductive plate or support surface 22. The electrosurgical generator 12 includes a transformer generally indicated as 24 including a primary and secondary coupled to an electrical source (not shown) to provide high frequency electrical energy to the plasma generator 14. Typically, the electrosurgical generator 12 comprises an isolated floating potential not referenced to any potential. Thus, current flows between the active and return electrodes. If the output is not isolated, but referenced to "earth", current can flow to areas with ground potential. If the contact surface of these areas and the patient is relatively small, an undesirable burning can occur.

The plasma generator 14 comprises a handpiece or holder 26 having an electrode 28 at least partially disposed within a fluid flow housing 29 and coupled to the transformer 24 to receive the high frequency electrical energy therefrom to at least partially ionize noble gas fed to the fluid flow housing 29 of the handpiece or holder 26 to generate or create the plasma stream 16. The high frequency electrical energy is fed from the secondary of the transformer 24 through an active conductor 30 to the electrode 28 (collectively active electrode) in the handpiece 26 to create the plasma stream 16 for application to the surgical site 18 on the patient 20. Furthermore, a current limiting capacitor 25 is provided in series with the electrode 28 to limit the amount of current being delivered to the patient 20.

The return path to the electrosurgical generator 12 is through the tissue and body fluid of the patient 20, the conductor plate or support member 22 and a return conductor 32 (collectively return electrode) to the secondary of the transformer 24 to complete the isolated, floating potential circuit.

In another embodiment, the electrosurgical generator 12 comprises an isolated non-floating potential not referenced to any potential. The plasma current flow back to the electrosurgical generator 12 is through the tissue and body fluid and the patient 20. From there, the return current circuit is completed through the combined external capacitance to the plasma generator handpiece 26, surgeon and through displacement current. The capacitance is determined, among other things, by the physical size of the patient 20. Such an electrosurgical apparatus and generator are described in commonly owned U.S. Pat. No. 7,316,682 to Konesky, the contents of which are hereby incorporated by reference in its entirety.

It is to be appreciated that transformer 24 may be disposed in the plasma generator handpiece 26, as will be described in various embodiments below. In this configuration, other transformers may be provided in the generator 12 for providing a proper voltage and current to the transformer in the handpiece 26, e.g., a step-down transformer, a step-up transformer or any combination thereof.

Figures 2A, 2B:
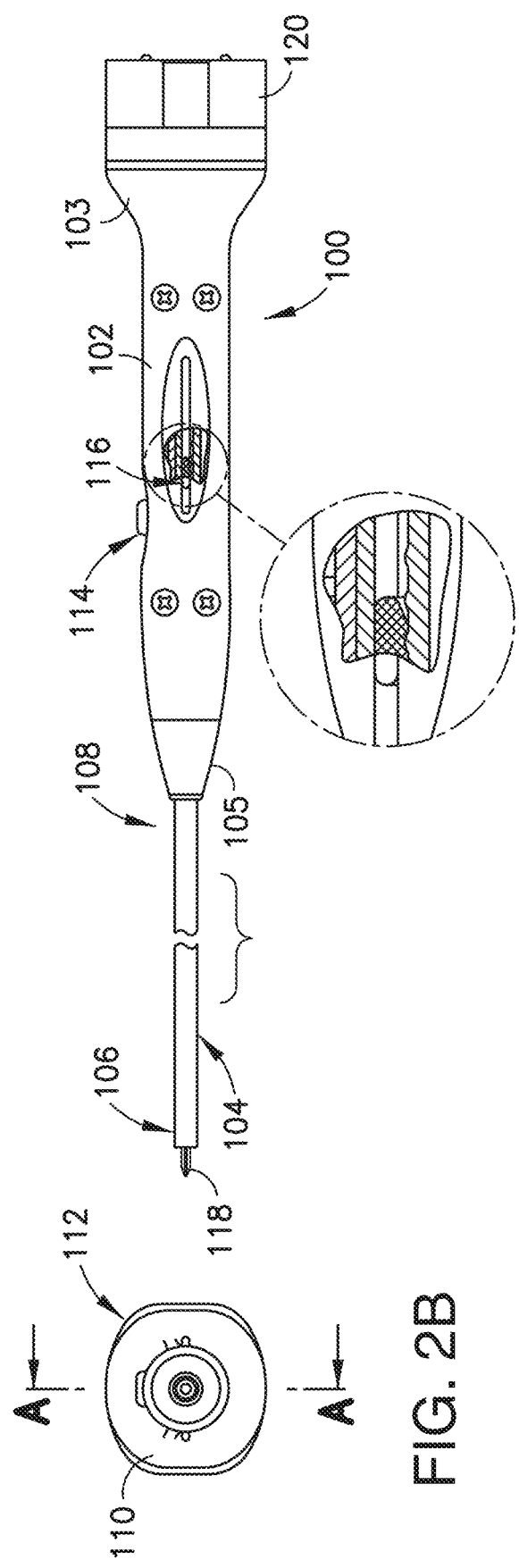
FIG. 2A is a schematic diagram showing a side view of an electrosurgical apparatus in accordance with an embodiment of the present disclosure.
FIG. 2B is a front view of the electrosurgical apparatus shown in FIG. 2A.
Figure 2C:
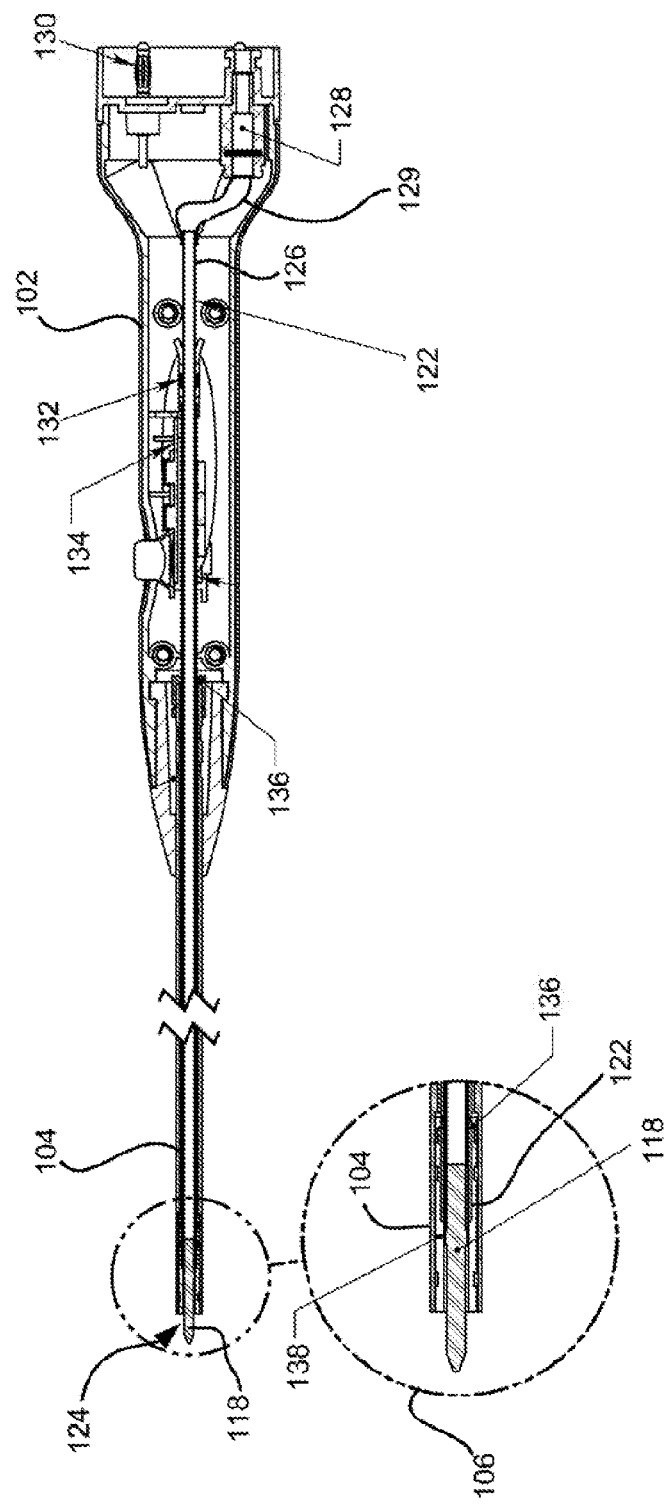
FIG. 2C is a cross sectional view of the electrosurgical apparatus shown in FIG. 2A taken along line A-A.

Referring to FIGS. 2A-2C, an electrosurgical apparatus 100 in accordance with the present disclosure is illustrated. Generally, the apparatus 100 includes a housing 102 having a proximal end 103 and a distal end 105 and a tube 104 having an open distal end 106 and a proximal end 108 coupled to the distal end 105 of the housing 102. The housing 102 includes a right side housing 110 and left side housing 112, and further includes provisions for a button 114 and slider 116. Activation of the slider 116 will expose a blade 118 at the open distal end 106 of the tube 104. Activation of the button 114 will apply electrosurgical energy to the blade 118 and, in certain embodiments, enable gas flow through the flow tube 122, as will be described in detail below.

Additionally, a transformer 120 may be provided on the proximal end 103 of the housing 102 for coupling a source of radio frequency (RF) energy to the apparatus 100. By providing the transformer 120 in the apparatus 100 (as opposed to locating the transformer in the electrosurgical generator), power for the apparatus 100 develops from higher voltage and lower current than that required when the transformer is located remotely in the generator, which results in lower thermalization effects. In contrast, a transformer back in the generator produces applicator power at a lower voltage, higher current with greater thermalization effects. Therefore, by providing the transformer 120 in apparatus 100, collateral damage to tissue at the operative site is minimized.

A cross section view along line A-A of the apparatus 102 is shown in FIG. 2C. Disposed within the housing 102 and tube 104 is flow tube 122 which runs along the longitudinal axis of the apparatus 100. On a distal end 124 of the flow tube 122, the blade 118 is retained within the flow tube 122. A proximal end 126 of the flow tube 122 is coupled to a source of gas via a tube connector 128 and flexible tubing 129. The proximal end 126 of the flow tube 122 is also coupled to a source of RF energy via plug 130 which couples to transformer 120. The flow tube 122 is made of an electrically conducting material, preferably stainless steel, as to conduct the RF energy to the blade 118 when being employed for plasma applications or electrosurgical cutting as will be described below. The outer tube 104 is constructed from non-conductive material, e.g., Lestran™. The slider 116 is coupled to the flow tube 122 via a retaining collar 132. A printed circuit board (PCB) 134 is disposed in the housing 102 and controls the application of the RF energy from the transformer 120 via the button 114.

It is to be appreciated that the slider 116 may be freely moveable in a linear direction or may include a mechanism for incremental movements, e.g., a ratchet movement, to prevent an operator of the apparatus 100 from over extending the blade 118. By employing a mechanism for incremental movements of the blade 118, the operator will have greater control over the length of the exposed blade 118 to avoid damage to tissue at the surgical site.

An enlarged view of the distal end 106 of the outer tube 104 is also illustrated in FIG. 2C. Here, the blade 118 is coupled to the flow tube 122 which is held in place in the outer tube 104 by at least one seal 136. The at least one seal 136 prevents backflow of gas into tube 104 and housing 102. A cylindrical ceramic insert 138 is disposed in the distal end of the outer tube 104 to maintain the blade along the longitudinal axis of the apparatus 100 and provide structural support during mechanical cutting when the blade is exposed beyond the distal end of the outer tube 104.

The operational aspect of the apparatus 100 will now be described in relation to FIGS. 3A and 3B, where FIG. 3A shows an enlarged cross section of the apparatus and FIG. 3B illustrates a front view of the apparatus.

Referring to FIG. 3A, the flow tube 122 is disposed in the outer tube 104 with a cylindrical insulator 140 disposed around the flow tube 122. Slider 116 is coupled to the insulator 140 and is employed to extend and retract the blade 118. At the distal end 106 of the outer tube 104, the annular or ring shaped seal 136 and cylindrical ceramic insert 138 are disposed about the flow tube 122. As can be seen In FIG. 3B, the generally planar blade 118 is coupled to an inner circumference of the cylindrical flow tube 122 such that two gas passageways 142, 144 are formed on the both sides of the blade 118. As gas flows from the proximal end 103 of the housing through the flow tube 122, the gas will pass over the blade 118 out the distal end of the outer tube 104.

When the blade is in the retracted position as shown in FIG. 3A, the apparatus 102 is suitable for generating plasma. In the retracted position, RF energy is conducted to a tip 146 of the blade 118 from an electrosurgical generator (not shown) via the flow tube 122. An inert gas, such as helium or argon, is then supplied through the flow tube 122 from either the electrosurgical generator or an external gas source. As the inert gas flows over the sharp point 146 of the blade 118 held at high voltage and high frequency, a cold plasma beam is generated.

Figure 4:
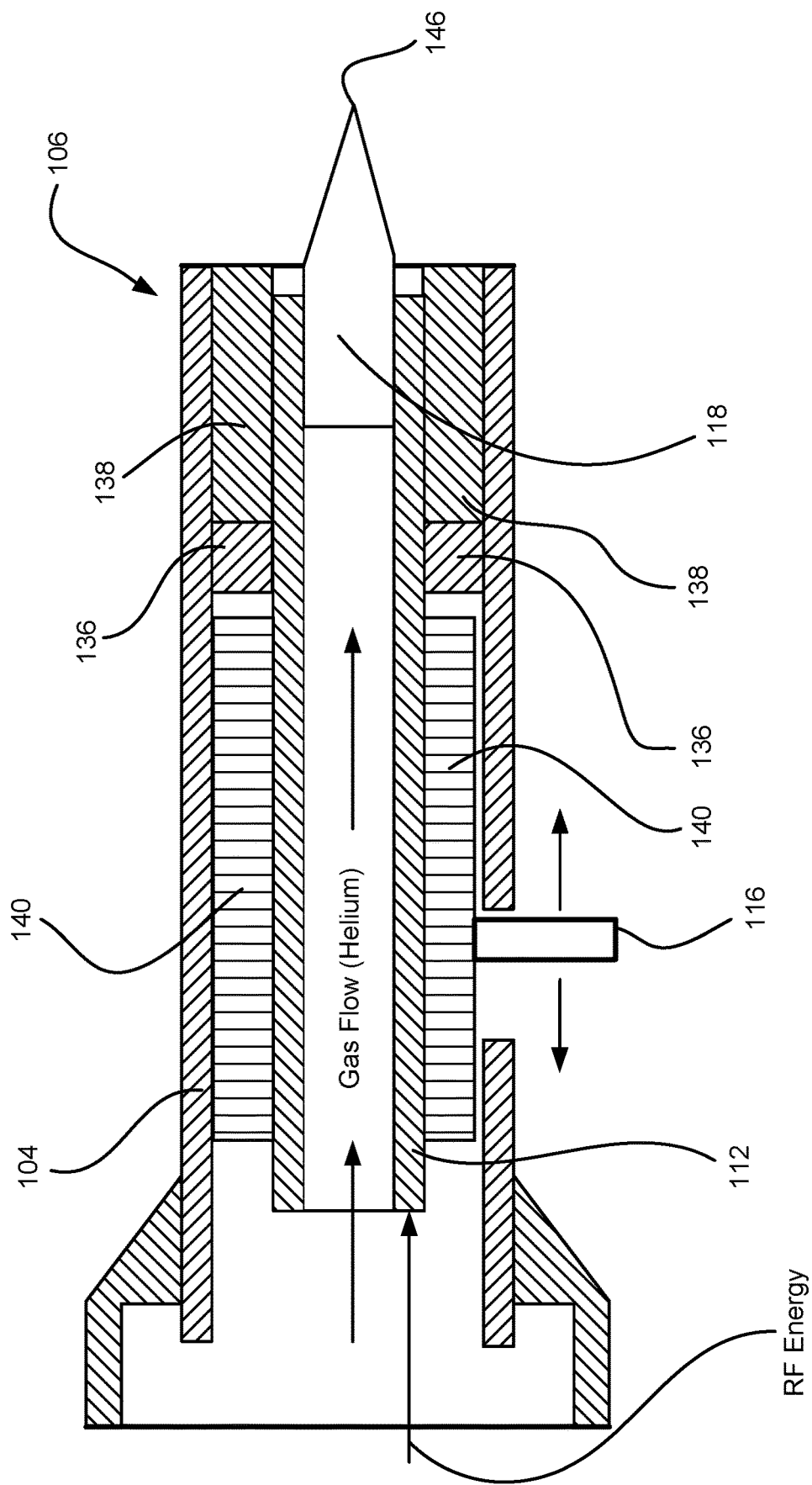
FIG. 4 is an enlarged cross sectional view of the electrosurgical apparatus shown in FIG. 3A with a blade extended.

Referring to FIG. 4, the blade 118 is advanced, via slider 116, so the tip 146 is extended pass the distal end 106 of the outer tube 104. In this state, the blade 118 can be used for two cutting modes: mechanical cutting and electrosurgical cutting. In the mechanical cutting mode, RF or electrosurgical energy is not applied to the flow tube 122 or blade 118, and therefore, the blade 118 is in a de-energized state. In this mode, the blade 118 can be used to excise tissue via mechanical cutting. After the tissue is removed, the blade 118 may be retracted via the slider 116 and electrosurgical energy and gas may be applied via button 114 to generate a cold plasma beam for cauterization, sterilization and/or hemostasis of the operative patient site.

In the electrosurgical cutting mode, the blade 118 is advanced and used while both electrically energized and enveloped with inert gas flow. This configuration resembles an electrosurgical knife approach, where the electrosurgical energy does the cutting. However, with the addition of the inert gas flow, cuts made show virtually no eschar, with very little collateral damage along the side walls of the cut. The cutting speed is considerably faster, with less mechanical cutting resistance as compared to when the knife blade is not electrically energized, i.e., the mechanical cutting mode. Hemostasis is also affected during this process.

Figure 5:
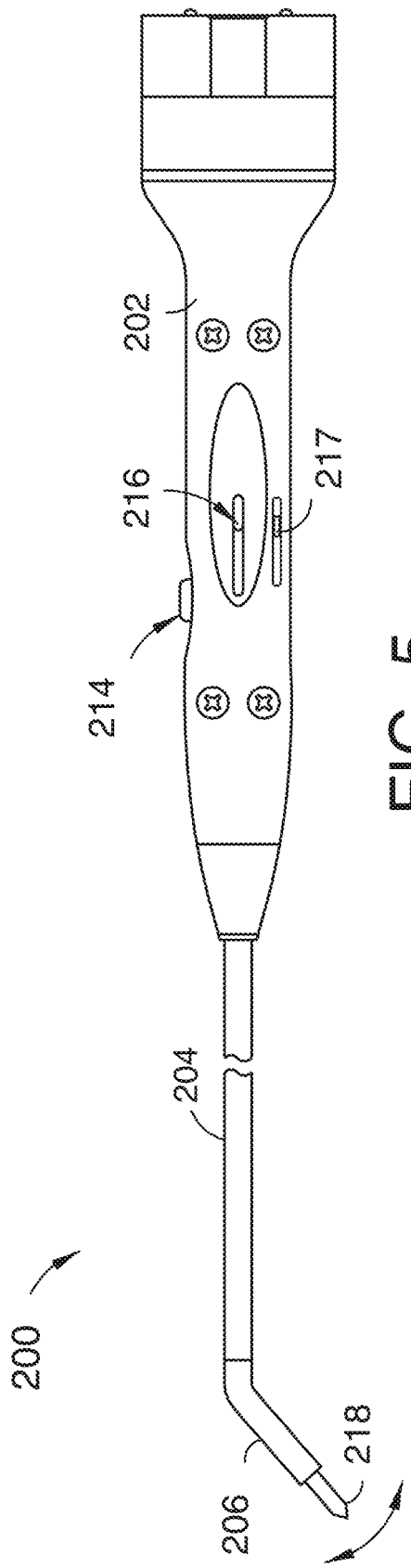
FIG. 5 illustrates an exemplary electrosurgical apparatus including an articulating distal end in accordance with an embodiment of the present disclosure.

In a further embodiment, the electrosurgical apparatus of the present disclosure will have an articulating distal end. Referring to FIG. 5, the electrosurgical apparatus 200 will have similar aspects to the embodiments described above. In this embodiment, however, the distal end 206, e.g., approximately 2 inches, is flexible to allow it to maneuver at the surgical site. An additional control 217, e.g., a slider, trigger, or the like, is provided in the proximal housing 202 to control the bending of the distal end 206. As in the above described embodiments, a button 214 is provided to apply electrosurgical energy to the blade 218 and, in certain embodiments, enable gas flow through the flow tube. Furthermore, slider 216 will expose the blade 218 at the open distal end 206 upon activation.

In one embodiment, the articulating control 217 will include two wires, one pulling to articulate and one pulling to straighten the distal end 206. The outer tube 204 will be the similar to the design shown in FIG. 2 and will be rigid, preferably made of Ultem™, Lestran™, or similar material, up to the last 2 inches which would be made of a material similar to that of a gastrointestinal (GI) flexible scope. In certain embodiments, a mesh infused Teflon™ or similar material and a flexible insulating material may be positioned inside the outer tube 204 and would allow the distal end 206 to bend at least 45° and not collapse the inner tube carrying the gas. The blade 218 will be made of a flexible metallic material such as Nitinol™ that would be able to bend but would retain its shape in the straightened position. Alternatively, a straight metal blade 218 would be provided with the distal 2 inches made of a linked metal, e.g., stainless steel, tungsten, etc., such that it would still carry a current but would be bendable and the cutting portion of the blade 218 would be attached to the distal end of the linked portion.

Figure 6A:
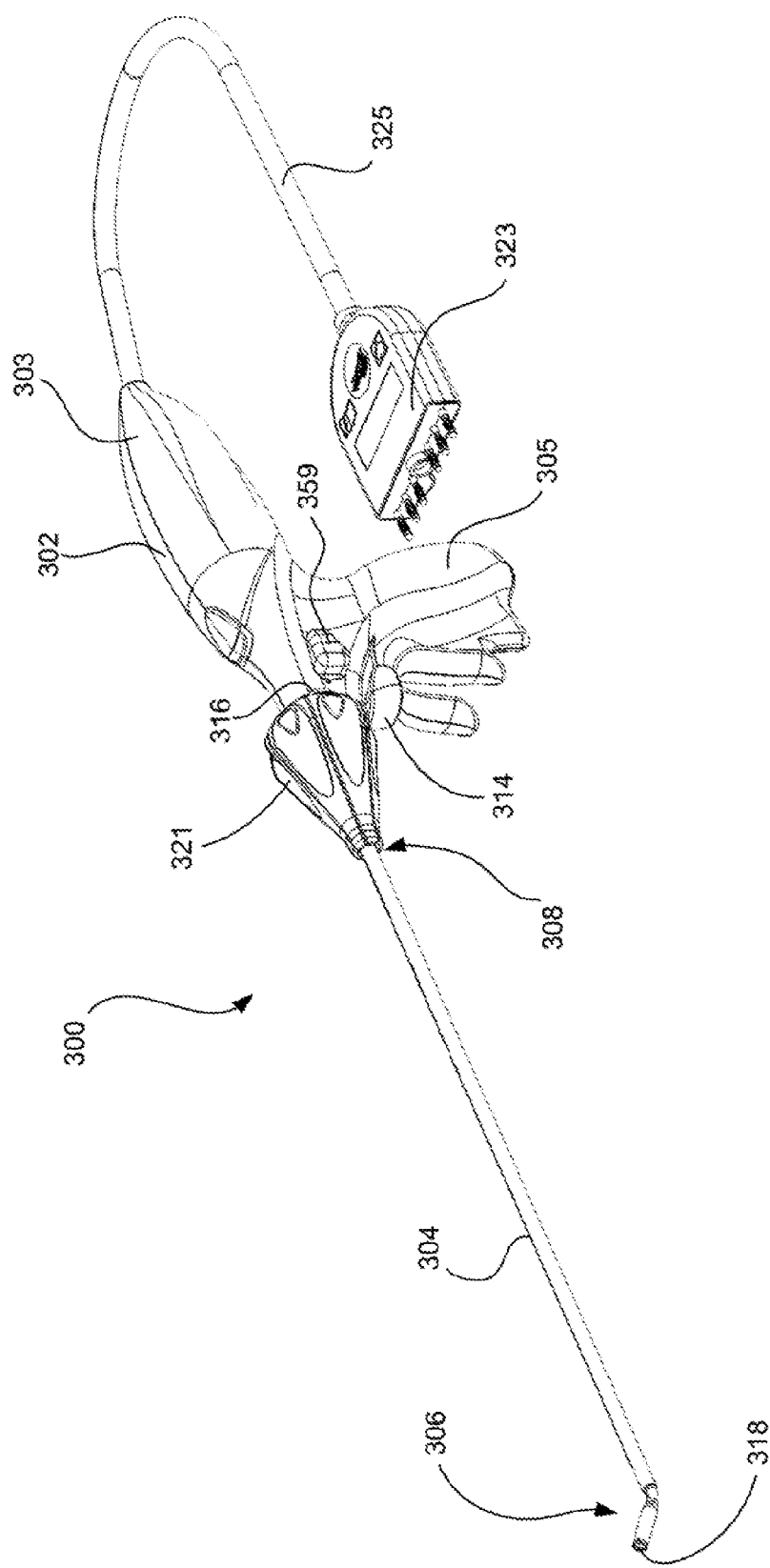
FIG. 6A is a perspective view of an electrosurgical apparatus in accordance with another embodiment of the present disclosure.

In another embodiment, an electrosurgical apparatus of the present disclosure includes a bent tip applicator. Referring to FIGS. 6A-6C, the electrosurgical apparatus 300 may be configured as a trigger-type handpiece or cold plasma bent tip applicator and will have similar aspects to the embodiments described above. In this embodiment, however, the distal end 306 is pre-bent, e.g., in certain embodiments approximately 28.72 mm, and rotatable to maneuver the distal end 306 at the surgical site 18. The electrosurgical apparatus 300 includes a housing 302 with a handle 305 to facilitate maneuvering of the apparatus by an operator. The electrosurgical apparatus 300 further includes a transformer 320 disposed in a proximal end 303 of the housing 302, an activation button 314 for activating the applicator or handpiece to generate plasma configured as a trigger-type button, an insulating tube 304 with a discharge electrode or blade 318 disposed therein. The discharge electrode or blade 318 is coupled to a conductive metal tube 322 which is further coupled to a slider button 316, collectively referred to as a slider assembly 319, which will be described in more detail below with reference to FIGS. 7A-7D. The slider button 316 moves the metal tube 322 which extends or retracts the discharge electrode or blade 318 beyond the distal end 306 of the insulating tube 304. A knob 321 is provided at the proximal end 308 of the insulating tube 304 to enable 360 degree rotation of the insulating tube 304 and thus the distal end 306 of the applicator. It is to be appreciated that the distal end 306 rotates at a predetermined angle relative to the longitudinal axis of the insulating tube 304. Additionally, a connector 323 is provided for coupling the applicator to an electrosurgical generator. In certain embodiments, the connector 323 receives electrosurgical energy and gas which it provides to the applicator or apparatus 300 via cable 325.

Figure 7A:
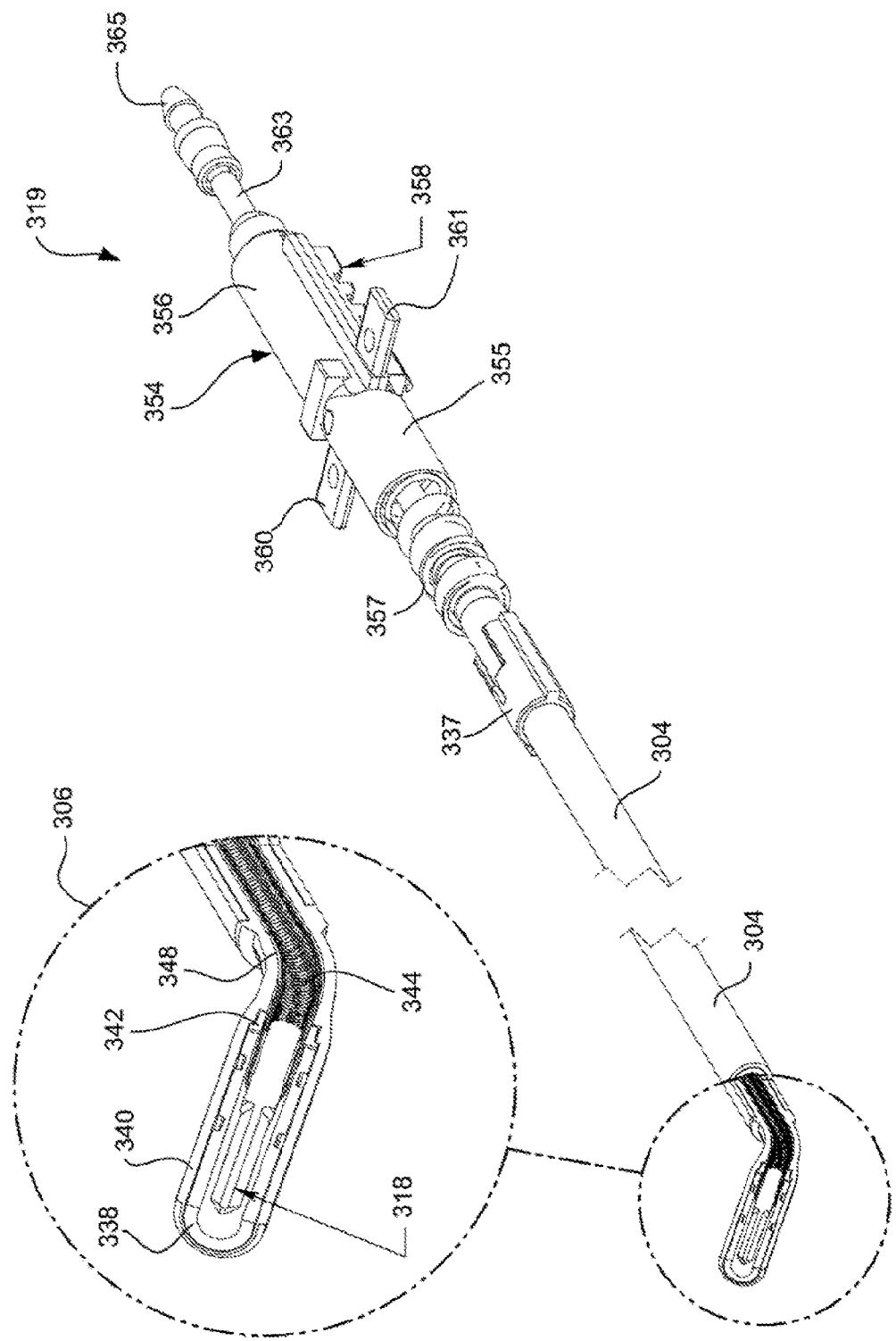
FIG. 7A is a perspective view of a slider assembly in accordance with an embodiment of the present disclosure.
Figure 7B:
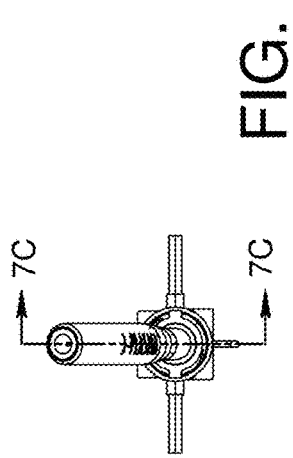
FIG. 7B is a front view of the electrosurgical apparatus shown in FIG. 7A.
Figure 7C:
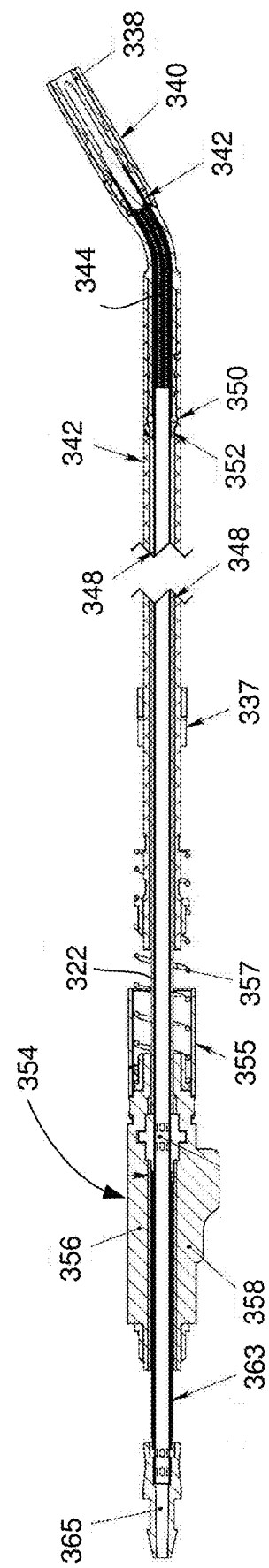
FIG. 7C is a cross sectional view of the slider assembly shown in FIG. 7B taken along line 7C-7C.
Figure 7D:
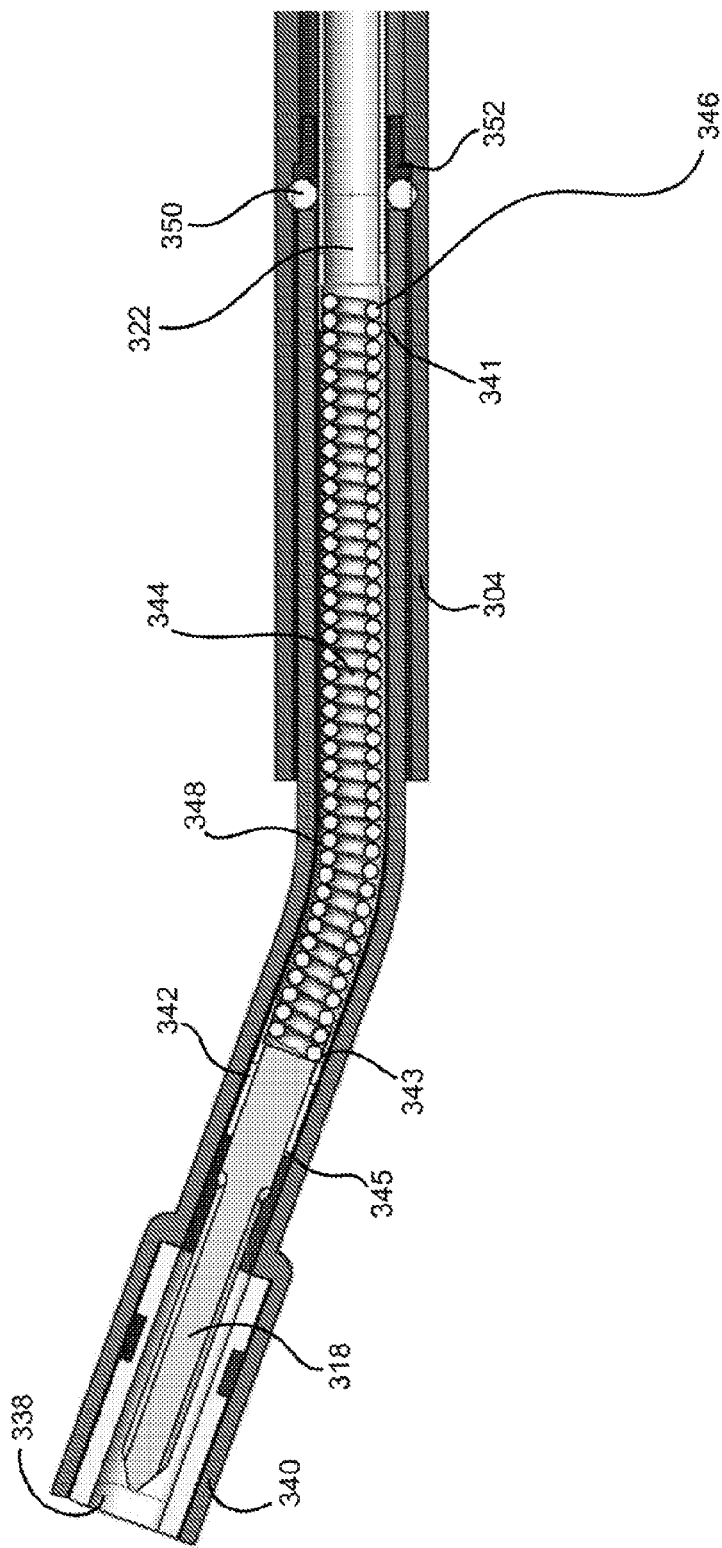
FIG. 7D is an enlarged cross sectional view of a distal end of the slider assembly shown in FIG. 7A.

Referring to FIGS. 7A-7D, the slider assembly 319 will be described in more detail, where FIG. 7A is a perspective view of the slider assembly 319, FIG. 7B is a front view of the slider assembly 319, FIG. 7C is a cross sectional view of the slider assembly 319, and FIG. 7D illustrates the internal construction of the distal end 306 of the slider assembly 319. Starting from the distal end 306 of the apparatus 300, a ceramic insert 338 is used to protect an outer tube distal housing 340 from potentially high temperatures when the device is used in the plasma beam generation mode. The outer tube distal housing 340 is formed from a shape memory polymer or material which retains its mechanical properties at high temperatures. An exemplary shape memory polymer includes a poly ether-ether ketone (PEEK) thermoplastic polymer, although other shape memory material is contemplated to be within the scope of the present disclosure. The outer tube distal housing 340, which has a slightly larger diameter adjacent to the ceramic insert 338, is sufficiently rigid to provide mechanical support for the tip assembly, yet flexible enough to accommodate the various bend angles that the tip may be preset to. An electrode or surgical blade 318 is housed within the outer tube housing 340 and attached to an adaptor tube 342 which connects to a spring 344. The proximal end 346 of the spring 344 is attached to the flow tube 322. It is to be appreciated that the coupling of components, e.g., between the spring 344 and flow tube 322 (generally denoted by reference numeral 341), between the spring 344 and adaptor tube 342 (generally denoted by reference numeral 343) and between the adaptor tube 342 and blade 318 (generally denoted by reference numeral 345), may be achieved by various methods including but not limited to laser welding.

A heat shrink tube 348, which may alternatively be configured as a flexible tube or wrap, is disposed around and firmly covers the spring 344. The heat shrink tube 348, flexible tube, or wrap provides a gas seal and also seals the spring 344 to the flow tube 322, i.e., the heat shrink tube 348 is provided at the junction of the spring 344 and flow tube 322 and extends over at least a portion of the flow tube 322. The spring/heat shrink tube combination is sufficiently flexible to allow an approximately 15 to 30 degree bend once the applicator tip emerges from the distal end of a trocar. It is to be appreciated that the result of the heat shrink tube 348 covering the spring 344 mimics the characteristics of the flow tube 322. This allows the passing of gas, e.g., through the flow tube 322 and heat shrink tube 348 and over the blade 318, without leaking out and enables flexibility through the 15 to 30 degree bent tip. It is to be appreciated that the heat shrink tube 348, covering tube, or wrap may be made from various materials which are insulating and gas impermeable, however are flexible enough to conform to the spring 344 to seal the spacings between coil turns and allow bending through various angles. It is further to be appreciated that other acute angles of the bent tip are contemplated to be within the scope of the present disclosure.

The flow tube 322, spring 344, and adaptor tube 342 all permit the flow of both inert gas and electrical energy to the surgical blade 318. An o-ring 350, optionally held in place by o-ring spacer 352, affects a gas seal and prevents inert gas leakage back into the housing 302 or handpiece. The outer tube housing 304, e.g., formed from Lestran™ or other suitable non-conductive material, provides both mechanical support for the entire assembly, and electrical safety insulation.

A retaining sleeve or anti-slip ring 337 is disposed on the tube 304. The anti-slip ring 337 engages the knob 321 to impact rotation to tube 304 and distal end 306, the details of which will be described below in relation to FIGS. 8C, 8D and 8E. A slider housing 354, including upper slider housing 356 and lower slider housing 358, is coupled to the flow tube 322. The slider housing 354 further includes wing members 360, 361 coupled to slider button 316 which is accessible on an outer surface of the housing 302. A barrier sleeve 355 is coupled to the slider housing 354 to retain a spring 357 disposed about the flow tube 322. In use, sliding the slider button 316 distally causes the flow tube 322 to move toward the distal end 306 of the applicator to extend the electrode 318 beyond the tip of the outer tube distal housing 340. To retract the electrode 318, a release button 359 is actuated where spring 357 drives the slider housing 354 toward the proximal end 308 of the applicator or tube 304.

An electrical contact 363, e.g., a copper contact, is disposed around the proximal end of the flow tube 322 and is coupled to an electrosurgical energy source for providing the electrosurgcial energy to the electrode 318. A gas flow coupler 365 is disposed on the proximal end of the flow tube for coupling to the cable 325 for providing gas to flow tube 322.

Figure 8A:
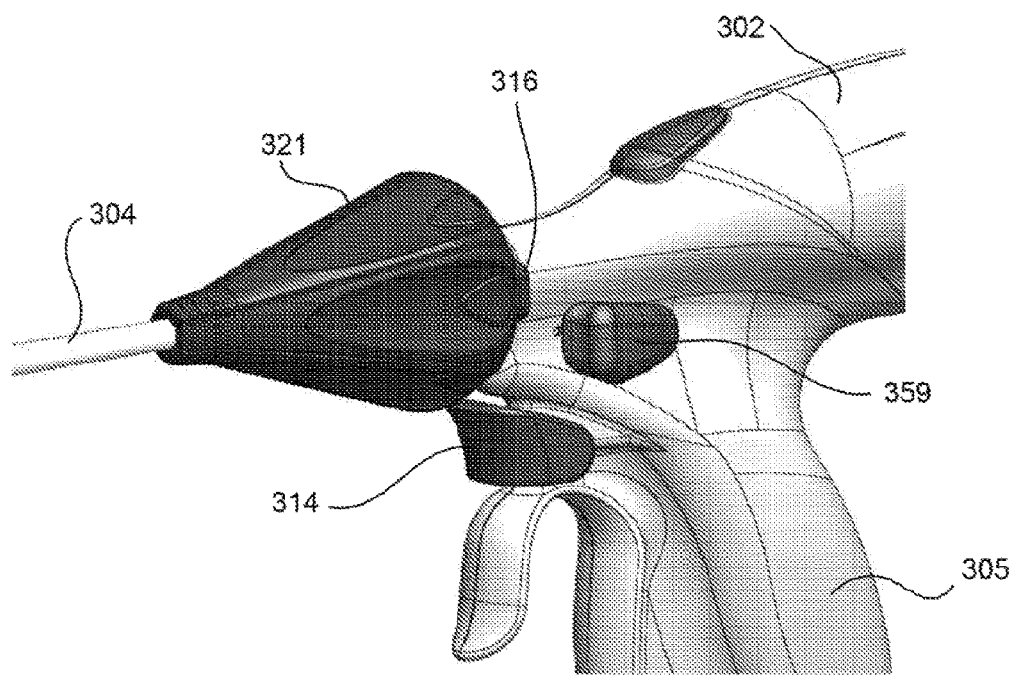
FIG. 8A is a partial view of the electrosurgical apparatus shown in FIG. 6.
Figure 8B:
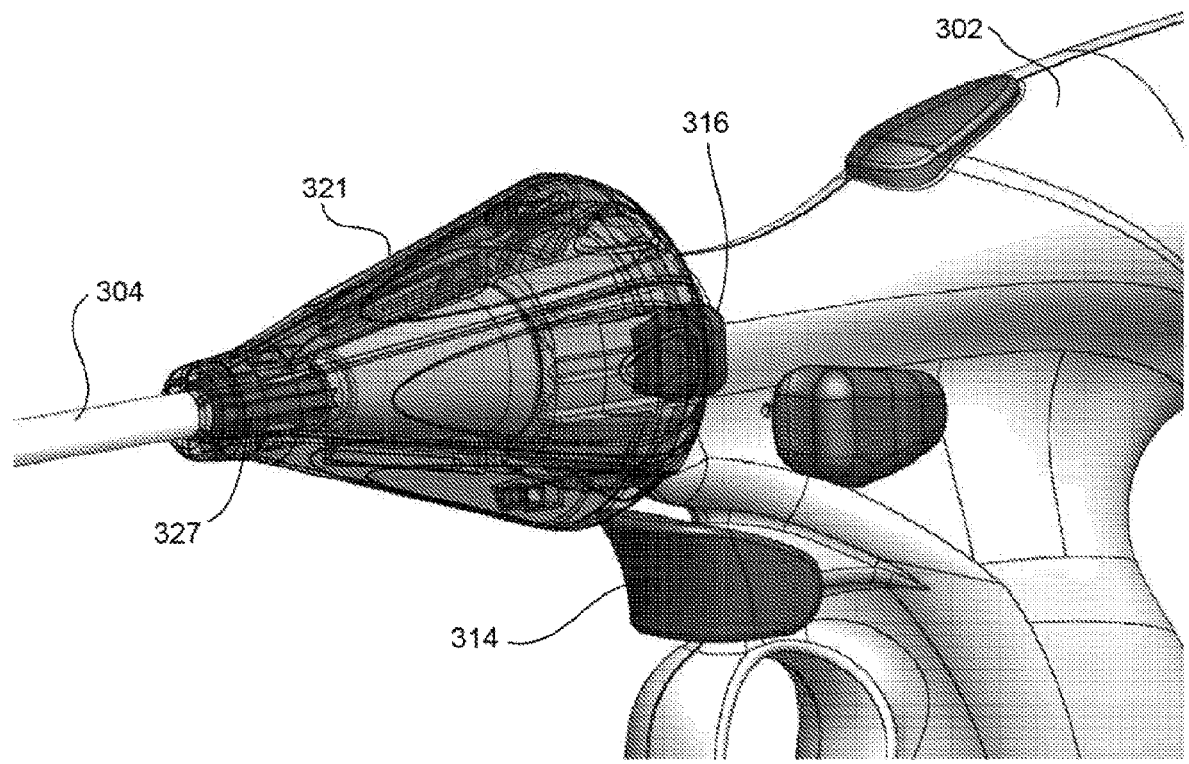
FIG. 8B is the partial view shown in FIG. 8A with a knob shown in phantom.
Figure 8C:
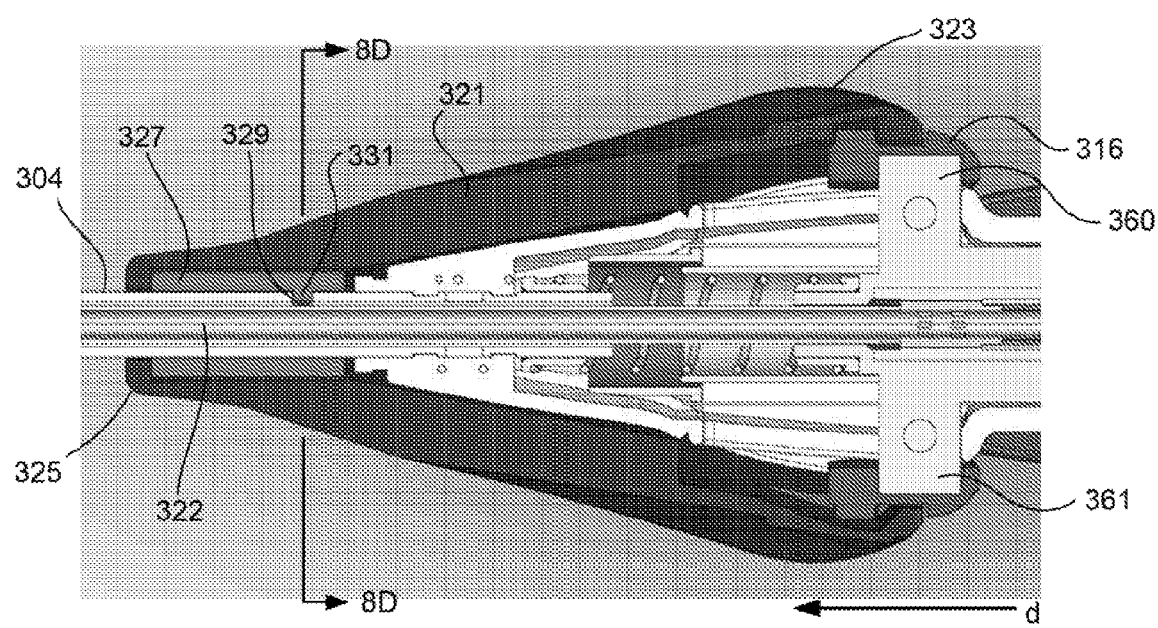
FIG. 8C a cross sectional view of a knob and slider of the electrosurgical apparatus in accordance with the present disclosure.
Figure 8D:
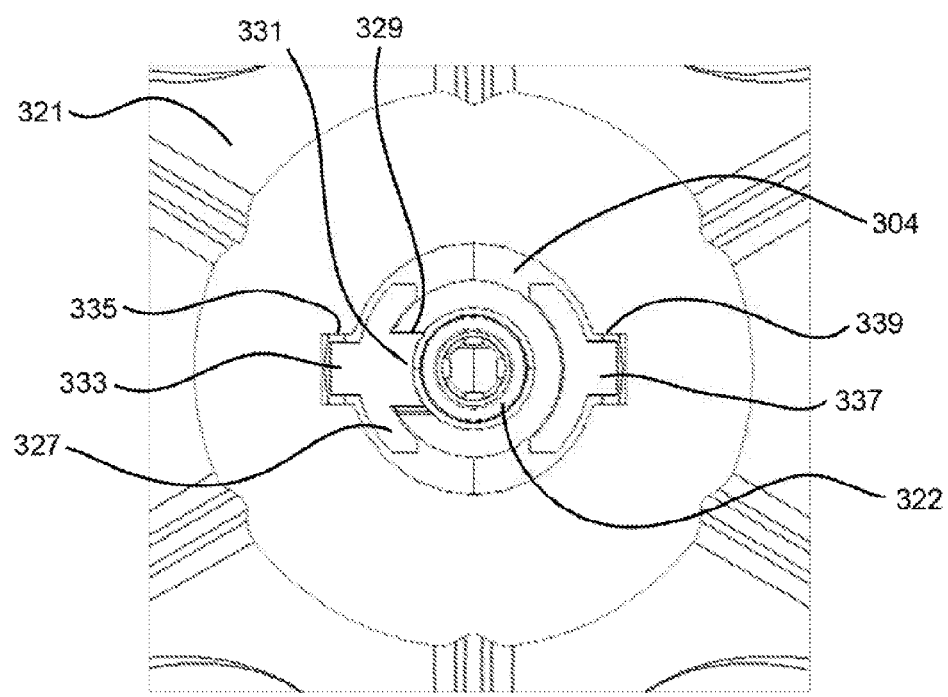
Figure 8E:
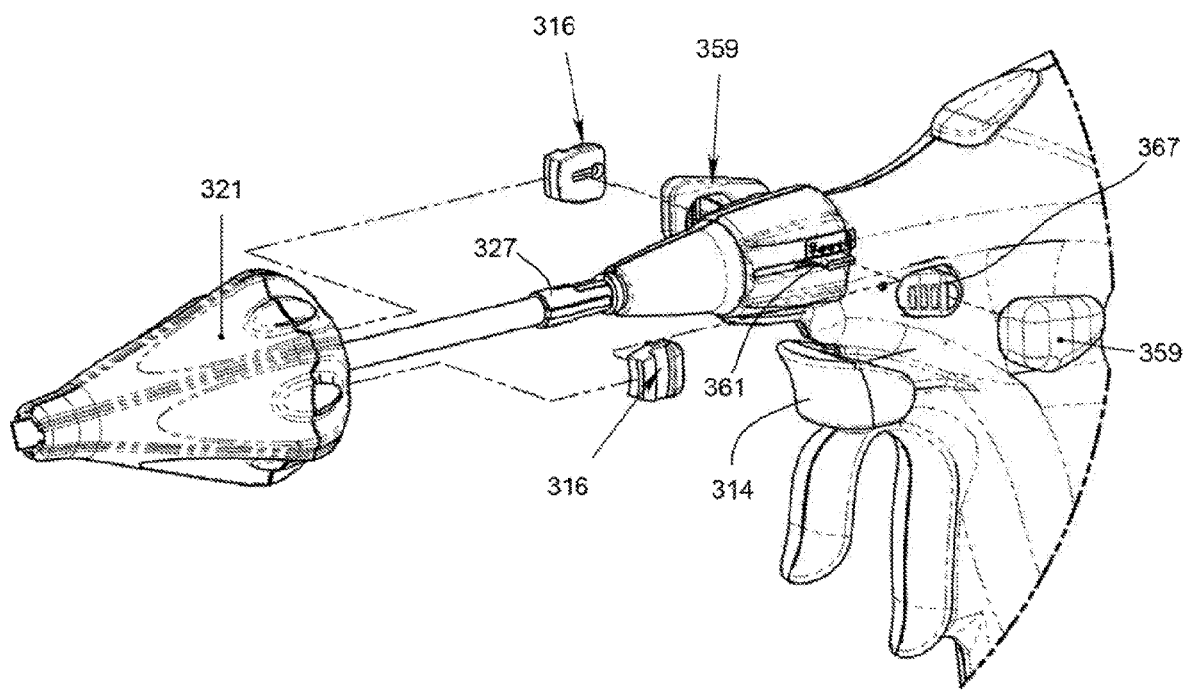
FIG. 8E is a partial exploded view of the electrosurgical apparatus shown in FIG. 8A showing the knob/slider details in accordance with an embodiment of the present disclosure.

FIG. 8A shows an example of the applicator attached to a housing or hand piece 302 which also allows full rotation of the distal end 306 of the applicator around 360 degrees. A rotation knob 321 on the hand piece 302 permits rotation of the entire bent tip of the distal end 306 and support tube assembly. The hand piece 302 also houses the various levers and pushbuttons to extend the surgical blade or electrode (e.g., via slider button 316), activate the application of electrical energy and gas flow (e.g., via trigger 314), retract the blade or electrode (e.g., via release button 359) and other user-defined functions, such as preset electrical power levels and gas flow rates.

Referring to FIGS. 8B through 8E, an operation of the knob 321 will be described. Knob 321 has a generally frustoconical shape including a proximal end 323 and a distal end 325. The proximal end 323 is coupled to the slider button 316 via, for example, a tongue and groove arrangement. The tongue and groove arrangement allows for the rotation of the knob 321 about the slider button 316. An anti-slip ring 327 (also known as a retaining sleeve) is fixedly coupled to the outer tube 304 via groove 329 and tab 331. The distal end 325 of the knob 321 makes contact with the anti-slip ring 327 to enable rotation of the outer tube 304. When the knob 321 is rotated, at least one rib or protrusion 333 on an outer surface of the ring 327 catches a groove 335 formed on the inner surface of the knob 321 to enable rotation.

When the knob 321 is rotated, the anti-slip ring 327 rotates and thus the outer tube 304 rotates, while the inner flow tube 322 is rotationally fixed. The outer tube 304 is fixedly coupled to the outer tube distal housing 340. As the outer tube distal housing 340 is rotated, the spring 344 and blade 318 float within the outer tube distal housing 340 to enable rotation of the distal end 306. That is, the spring 344 and blade 318 do not rotate and the blade 318 will remain in the same plane throughout the rotation of the outer tube distal housing 340, i.e., the plane of the blade will remain parallel to the plane of the handle 305 of the housing 302. For example, if the blade 318 is vertical, the blade 318 remains vertical at any rotated angle of the outer tube 304/outer tube distal housing 340.

The slider button 316 and knob 321 move together along the longitudinal axis of the apparatus to extend and retract the blade 318. When the slider button 316 is activated in the direction as indicated by arrow d, the knob 321 moves in the same direction sliding over the ring 327. The slider button 316 causes the inner flow tube 322 to move while the outer tube 304 remains in the same position. It is to be appreciated that the outer tube 304 moves rotationally but not in the direction of the longitudinal axis. Furthermore, it is to be appreciated that the inner flow tube 322 moves in the direction of the longitudinal axis but not rotationally. To retract the electrode 318, a release mechanism 367 is activated via the release button 359 to allow the spring 357 to drive the inner flow tube 322, via the slider housing 354, toward the proximal end 308 of the applicator.

Figure 9A:
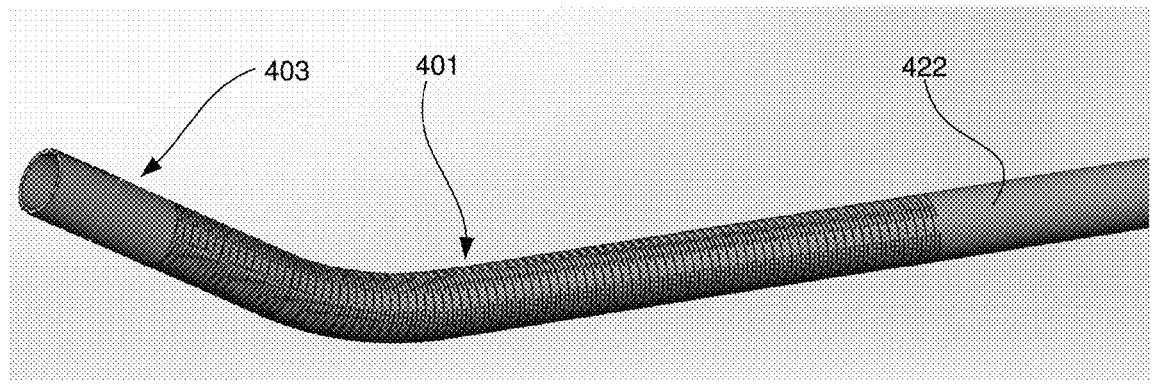
FIG. 9A illustrates an inner conductive tube in accordance with another embodiment of the present disclosure.
Figure 9B:
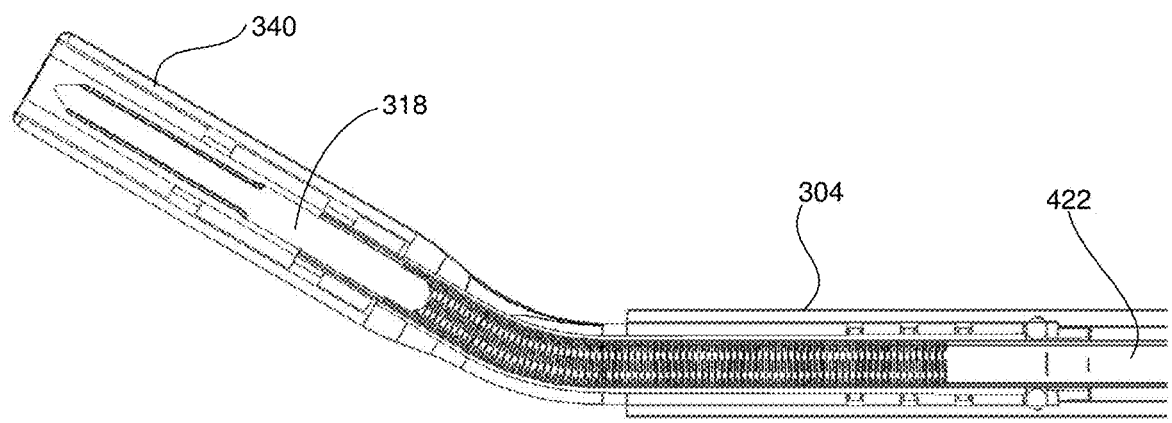
FIG. 9B is a cross sectional view of a distal end of the electrosurgical apparatus employing the inner conductive tube shown in FIG. 9A.

FIG. 9A illustrates another embodiment of an inner conductive tube 422 in accordance with the present disclosure. The inner conductive tube 422 includes a plurality of cuts 401, e.g., laser cuts, that enable a distal end 403 of the tube 422 to be flexible enough to allow rotation of the distal end 306 of the electrosurgical apparatus as described above. Referring to FIG. 9B, a cross sectional view of a distal end of the electrosurgical apparatus employing the inner conductive tube 422 shown in FIG. 9A is illustrated. The distal end 403 of the tube 422 is fixedly coupled to blade 318. The operation of the electrosurgical apparatus employing the tube 422 is similar to that described in relation to the embodiment shown in FIGS. 7 through 8C.

Figure 10A:
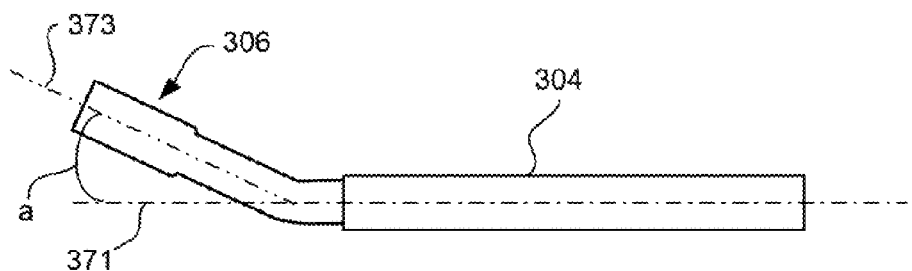
FIGS. 10A-10C illustrate an operation of the electrosurgical apparatus with the present disclosure, where
Figure 10B:
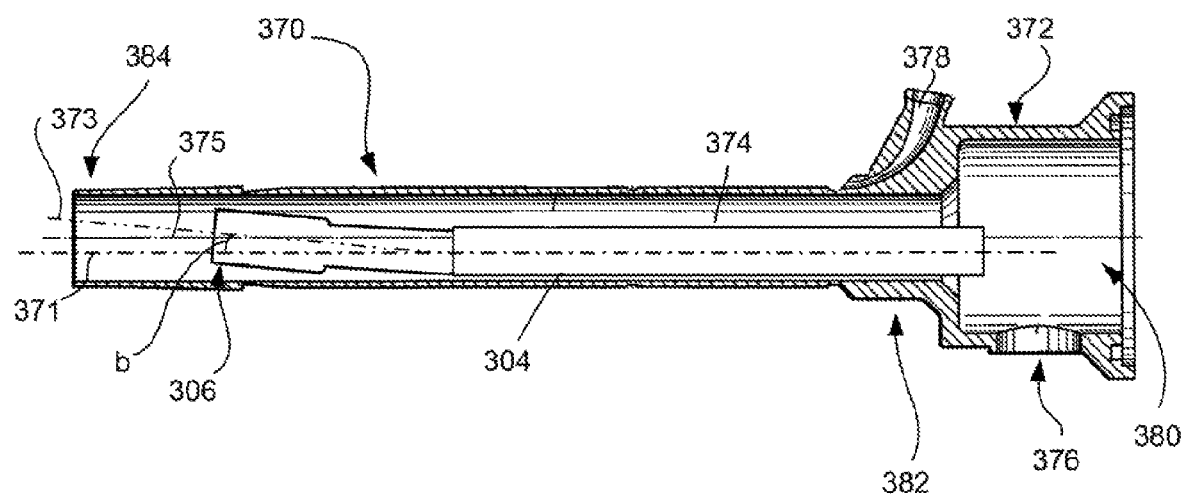
Figure 10C:
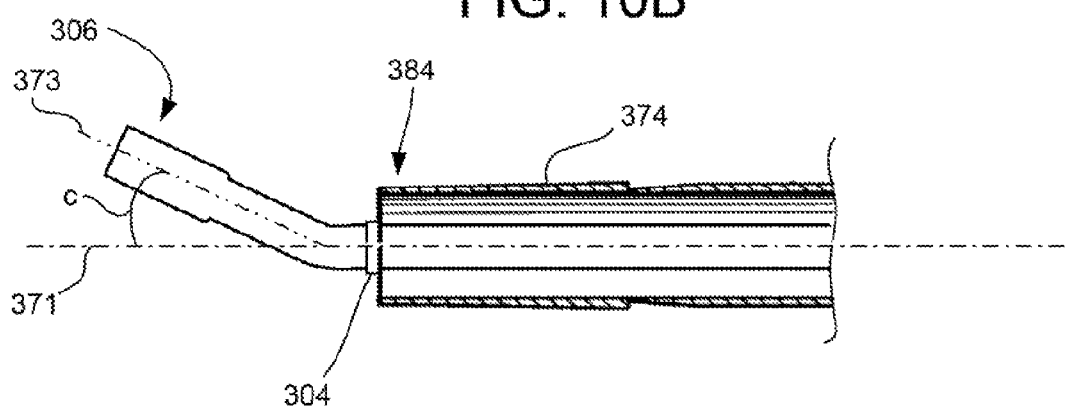

FIGS. 10A-10C illustrate an operation of an electrosurgical apparatus, such as apparatus 300, in accordance with the present disclosure, where FIG. 10A illustrates a distal end of the electrosurgical apparatus before insertion into a trocar, FIG. 10B illustrates the distal end of the electrosurgical apparatus passing through the trocar and FIG. 10C illustrates the distal end of the applicator emerging from the distal end of the trocar when fully inserted.

FIG. 10A illustrates the normal or unbiased state of the cold plasma applicator. As shown in FIG. 10A, the distal end 306 of the cold plasma applicator is pre-bent relative to the tube 304 at predetermined angle a, e.g., from about 0 degrees to about 20 degrees, although other angles are comtemplated to be within the scope of the present disclosure. As can be seen in FIG. 10A, a longitudinal axis 373 of the distal end 306 is pre-bent at an acute angle, e.g., angle a, relative to the longitudinal axis 371 of the tube 304. It is to be appreciated that the pre-bent angle is the normal or unstressed position of the distal end 306. The distal end 306 can be manipulated, or stressed, so the distal end 306 relative to the outer tube 304 can be at an angle less than the predetermined angle a so the applicator may pass through a trocar.

FIG. 10B illustrates an exemplary cannula or trocar 370, which includes a hub 372 connected to tubular member 374 aligned along a central axis 375. In certain embodiments, the hub 372 may include a port 376 for receiving valving and gas input components and a fluid input 378 for introduction of necessary or desired fluids to irrigate a surgical site. The hub 372 includes an opening 380 for receiving the cold plasma applicator 300 which is to be inserted into the tubular member 374. The tubular member 374 includes a proximal end 382 and a distal end 384. As shown in FIG. 10B, the distal end 306 of the cold plasma applicator 300 is straightened relative to the tube 304 at angle b, where angle b is less than angle a. It is to be appreciated that angle b is measured as the angle between the longitudinal axis 373 of the distal end 306 and the longitudinal axis 371 of the tube 304. With the distal end 306 at angle b, i.e., the biased or stressed state, the cold plasma applicator 300 is inserted into the opening 380 of trocar 370 and the distal end 306 and tube 304 will fit in the tubular member 374 of trocar 370. It is to be appreciated that with the longitudinal axis 373 of the distal end 306 at angle b, the outer tube distal housing 340 is substantially coaxial (or linear) with the outer tube 304.

Referring to FIG. 10C, after the distal end 306 of the cold plasma applicator 300 passes the opening at the distal end 384 of the trocar, the distal end 306 attempts to return to its pre-insertion state, i.e., the unstressed state. The distal end 306 moves to an angle c which is slightly less than the pre-insertion angle a. Angle c is measured as the angle between the longitudinal axis 373 of the distal end 306 and the longitudinal axis 371 of the tube 304. It is to be appreciated that angle c is less than angle a, but greater than angle b, i.e., a>c>b. Once the distal end 306 passes the opening at the distal end 384 of the trocar, the bent tip can then be externally rotated by a user or surgeon via knob 321 to more accurately be directed to the target tissue.

It is to be appreciated that the shape memory property of the outer tube distal housing 340 enables the distal end 306 of the applicator to be pre-bent to a predetermined angle most suitable for a particular procedure, straightened to an angle less than the predetermined angle to allow the applicator to be inserted into a trocar or the like, and returned to substantially the predetermined angle when at the surgical site. The various embodiments of the present disclosure enable an electrosurgical apparatus to redirect a plasma beam relative to the longitudinal axis of the insulating outer tube without the need of complicated and difficult to operate mechanisms. The electrosurgical apparatus of the present disclosure enables articulation and rotation of a distal end of the apparatus to direct, for example, a plasma beam, 360 degrees at various articulation angles.

It is further to be appreciated that by retracting the electrosurgical apparatus, e.g., apparatus 300, into the trocar 370 so that a small portion of the distal end 306 just extends beyond the distal end of the trocar 370 (e.g., approximately 1-5 mm), the outer distal housing 340 becomes substantially coaxial with the outer tube housing 304 and the apparatus may be employed to, for example, generate plasma, in a straight on configuration, i.e., in substantially the direction of the central axis of the trocar.

It is to be appreciated that the various features shown and described are interchangeable, that is a feature shown in one embodiment may be incorporated into another embodiment.

While the disclosure has been shown and described with reference to certain preferred embodiments thereof, it will be understood by those skilled in the art that various changes in form and detail may be made therein without departing from the spirit and scope of the disclosure as defined by the appended claims.

Furthermore, although the foregoing text sets forth a detailed description of numerous embodiments, it should be understood that the legal scope of the invention is defined by the words of the claims set forth at the end of this patent. The detailed description is to be construed as exemplary only and does not describe every possible embodiment, as describing every possible embodiment would be impractical, if not impossible. One could implement numerous alternate embodiments, using either current technology or technology developed after the filing date of this patent, which would still fall within the scope of the claims.

It should also be understood that, unless a term is expressly defined in this patent using the sentence "As used herein, the term '_____' is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. § 112, sixth paragraph.

What is claimed is:

1. An electrosurgical apparatus comprising:
a housing having a passage extending therethrough, the housing having a proximal end and a distal end;
an electrically conducting tube having a proximal end, a flexible portion and a distal end, at least the proximal end of the electrically conducting tube being disposed in the passage of the housing, the flexible portion disposed adjacent to the distal end of the electrically conducting tube and configured from a plurality of cuts in the electrically conducting tube to enable articulation of the distal end of the electrically conducting tube;
an insulating outer tube having a proximal end and a distal end, the insulating outer tube disposed around the electrically conducting tube with the proximal end of the insulating outer tube coupled to the distal end of the housing, the electrically conducting tube being movable along a longitudinal axis of the housing and insulating outer tube; and
an electrode coupled to the distal end of the electrically conducting tube, wherein, in a first position for electrosurgical cutting, the electrode extends beyond the distal end of the insulating outer tube and, in a second position, the electrode is retracted within the insulating outer tube and is energized via the electrically conducting tube to form plasma when an inert gas flows through the electrically conducting tube,
wherein the flexible portion of the electrically conducting tube and the insulating outer tube are configured at a predetermined acute angle with respect to the longitudinal axis of the insulating outer tube such that when stressed the distal end of the insulating outer tube and the electrode are at an angle other than the acute angle and when unstressed the distal end of the insulating outer tube and the electrode to return to approximately the acute angle.

2. The electrosurgical apparatus of claim 1, further comprising a flexible tube disposed over the plurality of cuts of the flexible portion of the electrically conducting tube to prevent gas leakage from the electrically conducting tube.

3. The electrosurgical apparatus of claim 1, wherein the electrode is an electrically conducting blade tapered to a point at a distal end of the electrically conducting blade.

4. The electrosurgical apparatus of claim 1, further comprising a slider member coupled to the electrically conducting tube for moving the electrically conducting tube along the longitudinal axis thereby extending and retracting the electrode.

5. The electrosurgical apparatus of claim 4, further comprising a slider button accessible on the housing, the slider button being coupled to the slider member for actuating the slider member along the longitudinal axis.

6. The electrosurgical apparatus of claim 5, further comprising a knob coupled to the insulating outer tube to effect rotation of the distal end of the insulating outer tube in 360 degrees of rotation.

7. The electrosurgical apparatus of claim 1, further comprising a knob coupled to the insulating outer tube to effect rotation of the distal end of the insulating outer tube in 360 degrees of rotation.

8. The electrosurgical apparatus of claim 1, wherein the distal end of the insulating outer tube is configured from a shape memory material.

9. An electrosurgical apparatus comprising:
an insulating outer tube having a longitudinal axis, a proximal end, and a distal end;
an outer tube distal housing having a proximal end and a distal end, the proximal end of the outer tube distal housing being fixed to the distal end of the insulating outer tube such the outer tube distal housing rotates with the insulating outer tube, the distal end of the outer tube distal housing extending from the insulating outer tube at an acute angle with respect to the longitudinal axis;
an electrically conducting tube having a proximal end and a flexible distal end, wherein the electrically conducting tube is disposed within the insulating outer tube and is moveable along the longitudinal axis of the insulating outer tube and the outer tube distal housing; and
an electrode coupled to the flexible distal end of the electrically conducting tube, wherein, in a first position, the electrode is disposed within the outer tube distal housing and, in a second position, the electrode extends at least partially beyond the distal end of the outer tube distal housing,
wherein the outer tube distal housing comprises a shape memory material that when stressed enables the outer tube distal housing, the flexible distal end of the electrically conducting tube and the electrode to be at an angle other than the acute angle and when unstressed enables the outer tube distal housing, the flexible distal end of the electrically conducting tube and the electrode to return to approximately the acute angle,
wherein the insulating outer tube and the outer tube distal housing are rotatable while the electrically conducting tube is rotationally fixed such that the electrode floats within the outer tube distal housing as the insulating outer tube is rotated.

10. The electrosurgical apparatus of claim 9, wherein, in the first position, the electrode is configured to create a plasma discharge at the distal end of the outer tube distal housing when the electrode is energized and when an inert gas flows through the electrically conducting tube.

11. The electrosurgical apparatus of claim 9, wherein the electrode includes an electrically conductive blade, and wherein, in the second position, the electrode is configured for electrosurgical cutting.

12. The electrosurgical apparatus of claim 9, wherein the flexible distal end of the electrically conducting tube includes a spring and a flexible tube disposed over the spring, wherein the spring is configured to electrically and mechanically couple the electrode to the flexible distal end of the electrically conducting tube, and wherein the flexible tube is configured to prevent gas leakage.

13. The electrosurgical apparatus of claim 12, further comprising a slider assembly coupled to the electrically conducting tube for moving the electrically conducting tube along the longitudinal axis of the insulating outer tube to thereby extend and retract the electrode.

14. The electrosurgical apparatus of claim 13, further comprising a knob coupled to the insulating outer tube to effect rotation of the outer tube distal housing in 360 degrees of rotation, the outer tube distal housing rotates at the predetermined acute angle with respect to the longitudinal axis of the insulating outer tube.

15. The electrosurgical apparatus of claim 9, wherein the flexible distal end of the electrically conducting tube includes a plurality of cuts to enable articulation.

16. The electrosurgical apparatus of claim 9, wherein the shape memory material is a shape memory polymer.

17. The electrosurgical apparatus of claim 9, further comprising a slider assembly coupled to the electrically conducting tube for moving the electrically conducting tube along the longitudinal axis of the insulating outer tube to thereby extend and retract the electrode.

18. The electrosurgical apparatus of claim 9, further comprising a knob coupled to the insulating outer tube to effect rotation of the outer tube distal housing in 360 degrees of rotation, the outer tube distal housing rotates at the predetermined acute angle with respect to the longitudinal axis of the insulating outer tube.

19. An electrosurgical apparatus comprising:
a housing having a passage extending therethrough, the housing having a proximal end and a distal end;
an electrically conducting tube having a proximal end and a distal end, at least the proximal end of the electrically conducting tube being disposed in the passage of the housing;
a first, insulating outer tube having a proximal end and a distal end, the first, insulating outer tube disposed around the electrically conducting tube with the proximal end of the first, insulating outer tube coupled to the distal end of the housing, the electrically conducting tube being movable along a longitudinal axis of the housing and the first, insulating outer tube;
a second, distal insulating outer tube coupled to the distal end of the first, insulating outer tube, the second, distal insulating outer tube configured at a predetermined acute angle with respect to the longitudinal axis of the first, insulating outer tube, the distal end of the electrically conducting tube being movable within the second, distal insulating outer tube; and
an electrode coupled to the distal end of the electrically conducting tube via a spring, the spring configured to electrically and mechanically couple the electrode to the distal end of the electrically conducting tube, wherein, in a first position for electrosurgical cutting, the electrode extends beyond a distal end of the second, distal insulating outer tube and, in a second position, the electrode is retracted within the second, distal insulating outer tube and is energized via the electrically conducting tube to form plasma when an inert gas flows through the electrically conducting tube,
wherein the second, distal insulating outer tube comprises a shape memory material that when stressed enables the second, distal insulating outer tube and the electrode to be at an angle other than the acute angle and when unstressed enables the second, distal insulating outer tube and the electrode to return to approximately the acute angle,
wherein the first, insulating outer tube and the second, distal insulating outer tube are rotatable while the electrically conducting tube is rotationally fixed such that the spring and electrode float within the second, distal insulating outer tube as the first, insulating outer tube is rotated.

20. The electrosurgical apparatus of claim 19, further comprising a flexible tube disposed over the spring, the flexible tube configured to prevent gas leakage from within the electrically conducting tube.

21. The electrosurgical apparatus of claim 20, wherein the flexible tube includes a shrink wrap material.

22. The electrosurgical apparatus of claim 19, wherein the electrode is an electrically conducting planar blade tapered to a point at a distal end of the electrically conducting planar blade, wherein when the first, insulating outer tube is rotated, the electrically conducting planar blade remains in the same plane throughout the rotation of the second, distal insulating outer tube.

23. The electrosurgical apparatus of claim 19, further comprising a slider member coupled to the electrically conducting tube for moving the electrically conducting tube along the longitudinal axis thereby extending and retracting the electrode.

24. The electrosurgical apparatus of claim 23, further comprising a slider button accessible on the housing, the slider button being coupled to the slider member for actuating the slider member along the longitudinal axis.

25. The electrosurgical apparatus of claim 19, further comprising a knob coupled to the first, insulating outer tube to effect rotation of the second, distal insulating outer tube in 360 degrees of rotation.

* * * * *